United States Patent
Rantala et al.

(12)

(10) Patent No.: US 6,831,189 B2
(45) Date of Patent: Dec. 14, 2004

(54) METHODS AND COMPOUNDS FOR MAKING COATINGS, WAVEGUIDES AND OTHER OPTICAL DEVICES

(75) Inventors: Juha A. Rantala, Oulu (FI); Arto L. T. Maaninen, Oulu (FI); Tiina J. Maaninen, Oulu (FI); Jarkko J. Pietikainen, Oulu (FI)

(73) Assignee: Silecs Oy, Espoo (FI)

( * ) Notice: Subject to any disclaimer, the term of this patent is extended or adjusted under 35 U.S.C. 154(b) by 110 days.

(21) Appl. No.: 10/041,343

(22) Filed: Jan. 8, 2002

(65) Prior Publication Data

US 2003/0166954 A1 Sep. 4, 2003

(51) Int. Cl.$^7$ .............................. C07F 7/04; C07F 7/08; C07F 7/02; C07F 7/22; C07F 7/24
(52) U.S. Cl. ........................ 556/478; 556/88; 556/89; 556/482
(58) Field of Search ......................... 556/88, 89, 478, 556/482

(56) References Cited

U.S. PATENT DOCUMENTS 4,481,366 A * 11/1984 Hiyama et al. ............. 556/431
6,255,515 B1 * 7/2001 Kato et al. .................. 556/478

* cited by examiner

Primary Examiner—Brian Davis

(74) Attorney, Agent, or Firm—Kubovcik & Kubovcik

(57) ABSTRACT

A method comprises reacting a compound of the general formula $R1_{4-m}MOR3_m$ wherein m is an integer from 2 to 4, R1 is selected from alkyl, alkenyl, aryl, alkynyl or epoxy, and wherein R1 is nonfluorinated, or fully or partially fluorinated; OR3 is alkoxy; and M is an element selected from group 14 of the periodic table; with a compound of the general formula R2M1 wherein R2 is selected from alkyl, alkenyl, aryl, alkynyl or epoxy, and wherein R2 is at least partially fluorinated; and M1 is an element from group I of the periodic table; so as to make a compound of the general formula $R1_{4-m}MOR3_{m-1}R2$. A similar method of the invention comprises reacting a compound of the general formula $R1_{4-m}MOR3_{m-n}X_n$ wherein m is an integer from 2 to 4, and n is an integer from 0 to 3 and is not greater than m; R1 is selected from alkyl, alkenyl, aryl, alkynyl or epoxy, and wherein R1 is nonfluorinated, or fully or partially fluorinated; OR3 is alkoxy; X is a halogen; and M is an element selected from group 14 of the periodic table; with a compound of the general formula R2M1, wherein R2 is selected from alkyl, alkenyl, aryl, alkynyl or epoxy, and wherein R2 is at least partially fluorinated; and M1 is an element from group I of the periodic table; so as to make a compound of the general formula $R2MR1_{4-m}OR3_{m-n}X_{n-1}$. These compounds thus formed can be further reacted to attach an additional Rx group, or hydrolyzed, alone or with one or more similar compounds, to form a material having a molecular weight of from 500 to 10,000, which material can be deposited on various substrates as a coating or deposited and patterned for a waveguide or other optical device components.

100 Claims, No Drawings

METHODS AND COMPOUNDS FOR MAKING COATINGS, WAVEGUIDES AND OTHER OPTICAL DEVICES

BACKGROUND OF THE INVENTION

Growing internet and data communications are resulting in the need for greater numbers and types of optical components within expanding optical networks. DWDM systems, or any system that utilizes light to transmit information, utilize a variety of components for creating, transmitting, manipulating and detecting light. Such optical device components, also referred to as optoelectronic or photonic components, often comprises at least a portion that is transmissive to light at particular wavelengths. Fibers and planar light guides are examples of passive light transmissive optical components within an optical network. However, light manipulators (components that modify, filter, amplify, etc. light within the optical network) also often have portions that are transmissive to light, as often do photodetectors and light emittors.

Regardless of the type of optical device component, it is usually desirable that a material is used that is highly transmissive to the wavelengths used to transmit information through the optical network. In addition to low optical absorbance, the material should preferably have low polarization dependent loss and have low birefringence and anisotropy, and low stress. It is also desirable that the material be easy to deposit or form, preferably at a high deposition rate and at a relatively low temperature. Once deposited or formed, it is desirable that the material can be easily patterned, preferably directly patterned without the need for photoresist and etching steps, and preferably patterned with small feature sizes if needed. Once patterned, the material should preferably have low surface and/or sidewall roughness. The material should also preferably be hydrophobic to avoid uptake of moisture once installed and in use, and be stable with a relatively high glass transition temperature (not degrade or otherwise physically and/or chemically change upon further processing or when in use).

Often, current materials used for making optical device components have some, but not all, of these characteristics. For example, inorganic materials such as silica are relatively stable, have relatively high glass transition temperatures have relatively low optical loss. However, silica materials often require higher deposition temperatures (limiting substrates and components on the substrates) and have lower deposition rates and cannot be directly patterned. Organic materials such as polymers can be deposited at lower temperatures and at higher deposition rates, but are relatively unstable and have lower glass transition temperatures. What are needed are materials for optical device components that have a larger number of the preferred characteristics set forth above.

SUMMARY OF THE INVENTION

A method comprises reacting a compound of the general formula $R1_{4-m}MOR3_m$ wherein m is an integer from 2 to 4, R1 is selected from alkyl, alkenyl, aryl, alkynyl or epoxy, and wherein R1 is nonfluorinated, or fully or partially fluorinated; OR3 is alkoxy; and M is an element selected from group 14 of the periodic table; with a compound of the general formula R2M1 wherein R2 is selected from alkyl, alkenyl, aryl, alkynyl or epoxy, and wherein R2 is at least partially fluorinated; and M1 is an element from group I of the periodic table; so as to make a compound of the general formula $R1_{4-m}MOR3_{m-1}R2$.

A similar method of the invention comprises reacting a compound of the general formula $R1_{4-m}MOR3_{m-n}X_n$ wherein m is an integer from 2 to 4, and n is an integer from 0 to 3 and is not greater than m; R1 is selected from alkyl, alkenyl, aryl, alkynyl or epoxy, and wherein R1 is nonfluorinated, or fully or partially fluorinated; OR3 is alkoxy; X is a halogen; and M is an element selected from group 14 of the periodic table; with a compound of the general formula R2M1, wherein R2 is selected from alkyl, alkenyl, aryl, alkynyl or epoxy, and wherein R2 is at least partially fluorinated; and M1 is an element from group I of the periodic table; so as to make a compound of the general formula $R2MR1_{4-m}OR3_{m-n}X_{n-1}$. These compounds thus formed can be further reacted to attach an additional Rx group, or hydrolyzed, alone or with one or more similar compounds, to form a material having a molecular weight of from 500 to 10,000, which material can be deposited on various substrates as a coating or deposited and patterned for a waveguide or other optical device components.

DESCRIPTION OF THE PREFERRED EMBODIMENTS

Compounds

In the present invention, compounds are made that can be hydrolyzed and condensed (alone or with one or more other compounds) into a material having a molecular weight of from 500 to 10,000 (preferably from 1,000 to 3,000), which material can be deposited by spin-on, spray coating, dip coating, or the like. Such compounds are preferably partially or fully fluorinated, though not necessarily so in all embodiments. The compounds will preferably have an element M selected from groups 3–6 or 13–16 of the periodic table, which element is preferably tri-, tetra- or penta-valent, and more preferably tetravalent, such as those elements selected from group 14 of the periodic table. Connected to this element M are from three to five substituents, wherein from one to three of these substituents are organic groups to be discussed further below, with the remainder being a halogen or an alkoxy group.

Compound Example I

In one embodiment of the invention, a compound is provided of the general formula: $R^1MOR^3_3$, where $R^1$ is any partially or fully fluorinated organic group (preferably a partially or fully fluorinated aryl, alkenyl, alkynyl or alkyl group), where M is an element selected from column 14 of the periodic table, and where $OR^3$ is an alkoxy group—except where M is Si, $R^1$ is perfluorinated phenyl or perfluorinated vinyl, and $OR^3$ is ethoxy, which, though not novel per se, can be part of one of the novel methods of the invention as will be discussed further below. $R^1$ can have an inorganic component, though if so, a portion should preferably be a partially or fully fluorinated organic component. In a more preferred example of this embodiment, $R^1$ comprises a double bond that is capable of physical alteration or degradation in the presence of an electron beam, or electromagnetic radiation and a photo initiator (or sensitizer, photoacid or thermal initiator—to be discussed further below). In this example, $R^1$ could be an alkenyl group such as a vinyl group, or could be an epoxy or acrylate group, that is preferably partially or fully fluorinated. Such a group, as will be discussed further herein, can allow for crosslinking upon application of an electron beam or preferably electromagnetic radiation (e.g. directing ultraviolet light through a mask with the material comprising a photoinitiator). In the alternative, $R^1$ could be an organic group that is (or a hybrid organic-inorganic group that comprises) a single or multi ring structure (an "aryl group") or an alkyl group of any length, such as from 1 to 14 carbon atoms or longer (preferably 4–10)—the alkyl group capable of being a straight or branched chain. If $R^1$ is a ring structure, or a carbon chain of sufficient length (e.g. 4 (or 5) or more carbons), then such an $R^1$ group can provide bulk to the final material once hydrolyzed, condensed and deposited on a substrate. If $R^1$ is a ring structure, whether single ring or multi ring, it can have substituents thereon, fluorinated, though not necessarily, such as alkyl or alkenyl substituents (preferably from 1 to 5 carbons), and where the substituents on the ring structure can be at from 1 to 3 locations around the ring. $R^1$ can be a 4 to 8 sided ring structure (preferably 5 or 6 sided) which ring structure could comprise N or O. R1 could comprise nitrogen, or $R^1$ can also have an oxygen component, such as a carboxylate group (e.g. acrylate, butenecarboxylate, propenecarboxylate, etc.).

In the example above, in $R^1MOR^3{}_3$, M can be a tetravalent element from column 14 of the periodic table (e.g. Si or Ge), or a tetravalent element from column 16—e.g. Se (or a tetravalent early transition metal—such as titanium or zirconium). Also, $OR^3$ is an alkoxy group, though preferably one having from 1 to 4 carbon atoms (longer alkoxy groups can be used, but are more expensive). Specific examples include:

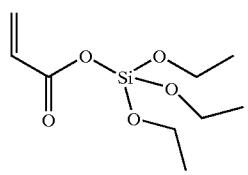

Acryltriethoxysilane

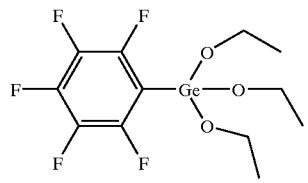

Pentafluorophenyltriethoxygermane

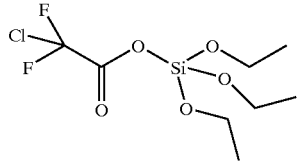

Chlorodifluoroacetic acid, triethoxysilyl ester

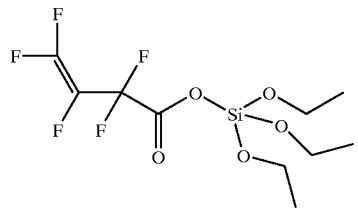

Perfluoro-3-butene acid, triethoxysilyl ester

-continued

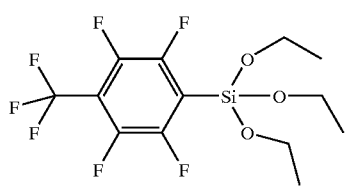

Heptafluorotoluenetriethoxysilane

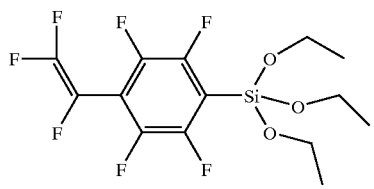

4-triethoxysilyl perfluorostyrene

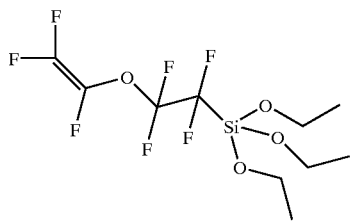

Tetrafluoroethyltrifluorovinyl ether triethoxysilane

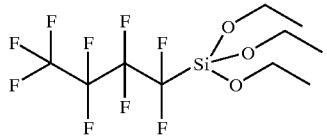

Perfluorobutanetriethoxysilane

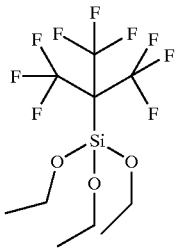

Perfluoro-t-butyl triethoxysilane

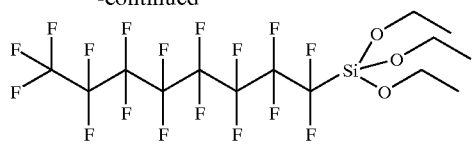

Perfluorooctyltriethoxysilane

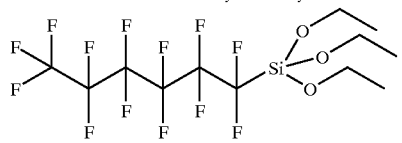

Perfluorohexanetriethoxysilane

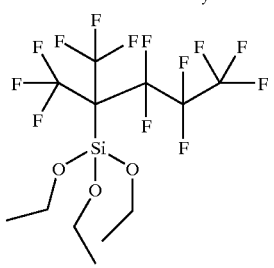

2-trifluoromethyl-2-triethoxysilyl perfluoro pentane

Compound Example II

In yet another embodiment of the invention, a compound is provided of the general formula: $R^1MOR^3{}_2X$, where $R^1$ is any partially or fully fluorinated organic group (preferably a partially or fully fluorinated aryl, alkenyl, alkynyl or alkyl group) as set forth above, where M is an element selected from group 14 of the periodic table as mentioned above, where X is a halogen, and where $OR^3$ is an alkoxy group as above. X in this example is preferably F, Cl, Br or I, and more preferably Cl or Br. Specific examples of compounds within this category include

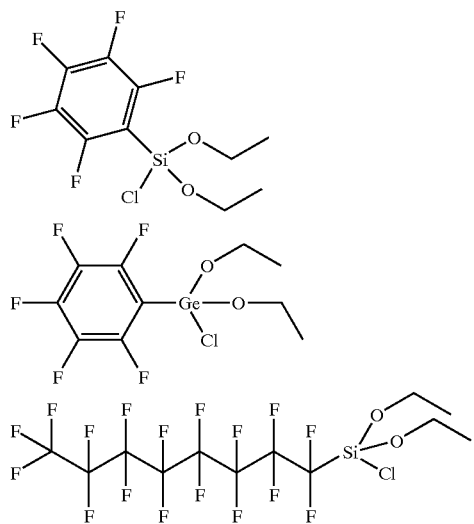

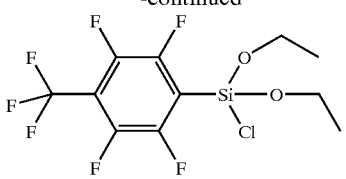

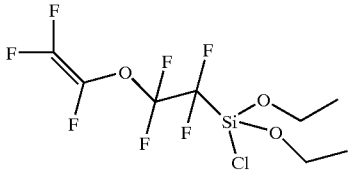

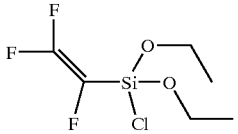

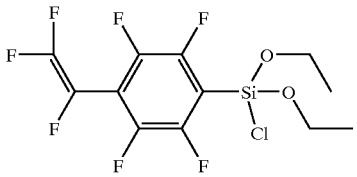

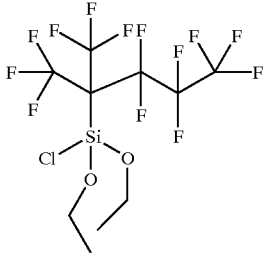

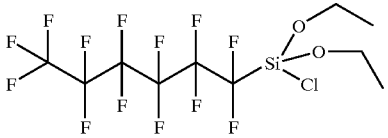

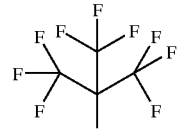

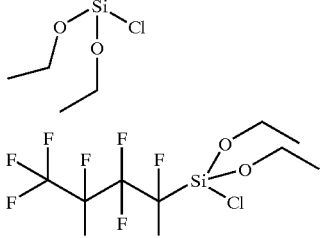

Compound Example III

In another embodiment of the invention, a compound is provided of the general formula: $R^1MX_2OR^3$, where $R^1$ is any partially or fully fluorinated organic group (preferably a partially or fully fluorinated aryl, alkenyl, alkynyl or alkyl group) as set forth above, where M is an element selected from group 14 of the periodic table as mentioned above, where $OR^3$ is an alkoxy group as above, and where X is a halogen as above—Except where M is Si, $R^1$ is perfluorinated phenyl, X is Cl, and OR³ is ethoxy, which, though not novel per se, is novel when used as part of the methods of the invention as will be discussed further below. Specific examples within this category include

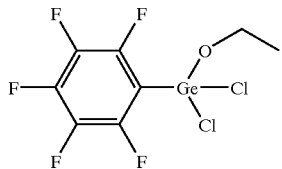

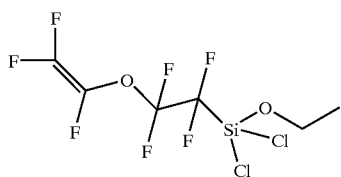

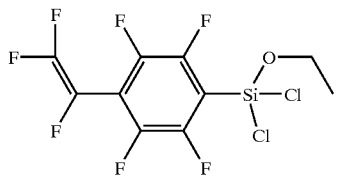

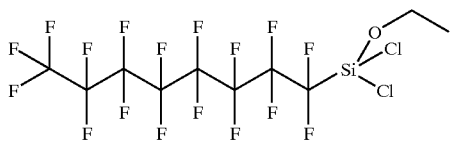

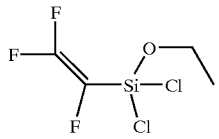

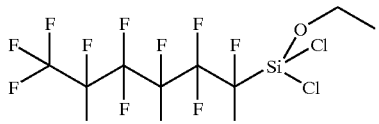

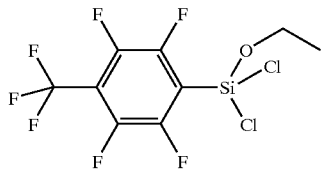

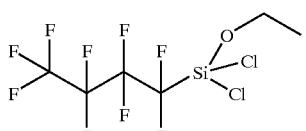

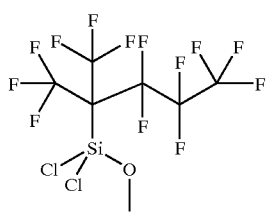

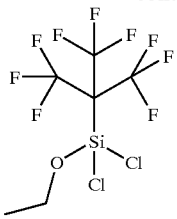

-continued

Compound Example IV

In a further embodiment of the invention, a compound is provided of the general formula: R¹MX₃, where R¹ is any partially or fully fluorinated organic group (preferably a partially or fully fluorinated aryl, alkenyl, alkynyl or alkyl group) as set forth above, where M is an element selected from group 14 of the periodic table as mentioned above, and where X is a halogen as above—Except where M is Si, R¹ is perfluorinated phenyl, perfluorinated methyl or perfluorinated vinyl, and X is Cl, which, though not novel per se, are novel when used as part of the methods of the invention as will be discussed further below. (f M is Si and X is Cl, some of these novel trichlorosilanes could be used for forming self assembled monolayers for making a surface hydrophobic, preferably by application in the vapor phase to a surface made of silicon and having OH end groups and moisture.) Specific examples within this category include

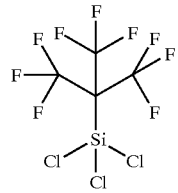

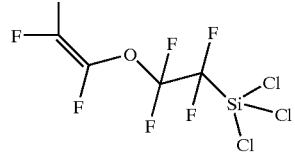

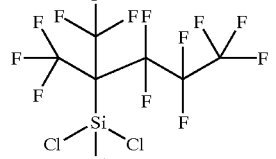

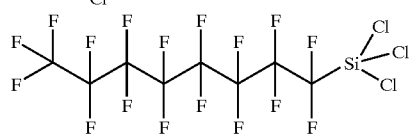

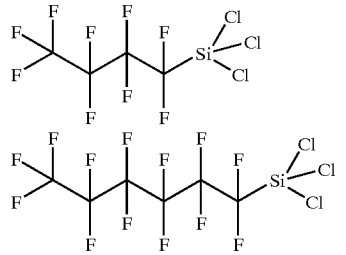

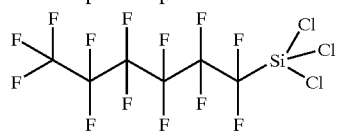

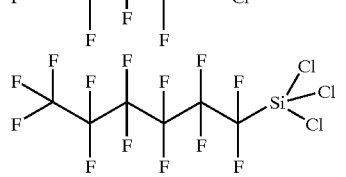

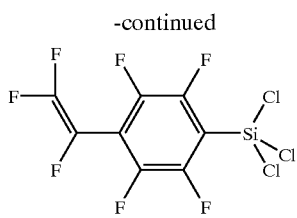

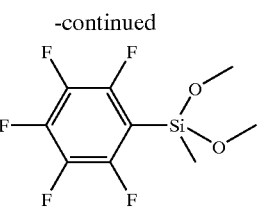

Methylpentafluorophenyldimethoxy-silane

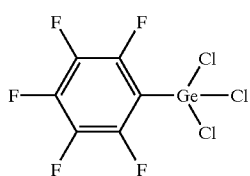

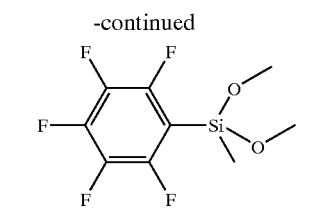

Pentafluorophenyltrifluoromethyldiethoxysilane

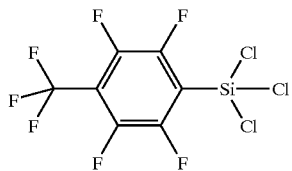

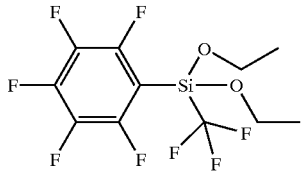

Perfluorotoluenetrifluorovinyldiethoxy-silane

Compound Example V

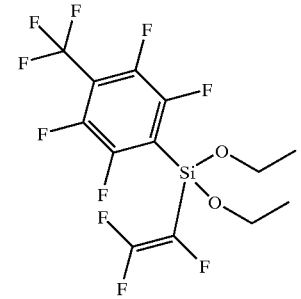

Di(perfluorotoluene)diethoxysilane

In yet another embodiment of the invention, a compound is provided of the general formula: $R^1R^2MOR^3{}_2$, where $R^1$ is any partially or fully fluorinated organic group (preferably a partially or fully fluorinated aryl, alkenyl, alkynyl or alkyl group) as set forth above with respect to $R^1$, $R^2$ is any partially or fully fluorinated organic group (preferably a partially or fully fluorinated aryl, alkenyl, alkynyl or alkyl group) as set forth above with respect to $R^1$, or any such organic groups nonfluorinated, and where $R^1$ and $R^2$ are the same or different from each other, where M is an element selected from group 14 of the periodic table as mentioned above, and where $OR^3$ is an alkoxy group as above—except where M is Si, $OR^3$ is ethoxy and $R^1$ and $R^2$ are perfluorinated phenyl groups, which compound is not novel per se, but is novel when used as part of the methods of the invention as set forth below. Specific examples within this category include:

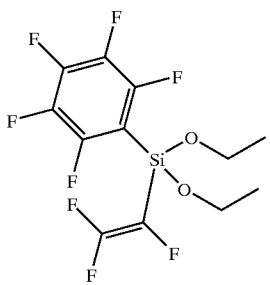

Pentafluorophenyltrifluorovinyldiethoxy-silane

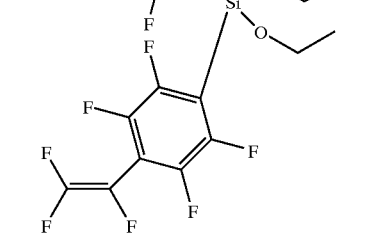

Perfluorostyreneperfluorotoluenediethoxy-silane

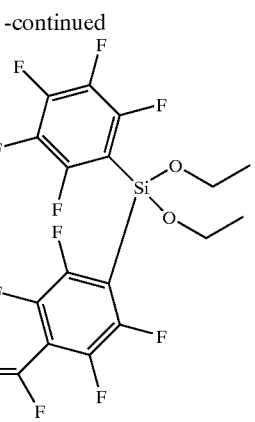

Pentafluorophenylperfluorostyryl-diethoxysilane

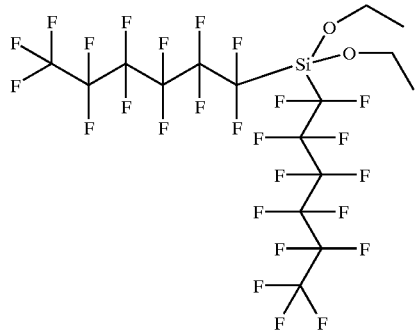

Bis(perfluorohexane)diethoxysilane

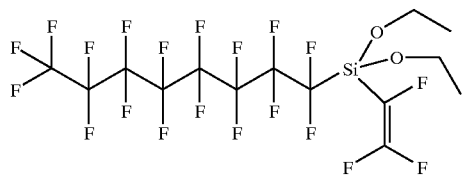

Perfluorooctyltrifluorovinyldiethoxysilane

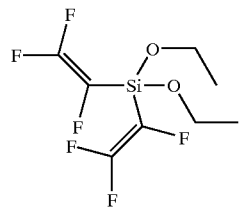

Bis(trifluorovinyl)diethoxysilane

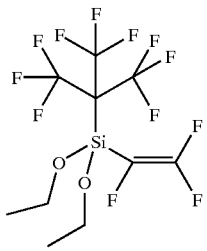

Perfluoro(t-butyl)trifluorovinyldiethoxysilane

Compound Example VI

In another embodiment of the invention, a compound is provided of the general formula: $R^1R^2MXOR^3$, where $R^1$ is any partially or fully fluorinated organic group (preferably a partially or fully fluorinated aryl, alkenyl, alkynyl or alkyl group) as set forth above with respect to $R^1$, $R^2$ is any partially or fully fluorinated organic group (preferably a partially or fully fluorinated aryl, alkenyl, alkynyl or alkyl group) as set forth above with respect to $R^1$, or any such organic groups nonfluorinated, and where $R^1$ and $R^2$ are the same or different from each other, where M is an element selected from group 14 of the periodic table as mentioned above, where $OR^3$ is an alkoxy group as above, and where X is a halogen. $R^1$ and $R^2$ can be the same or different from each other. Specific examples within this category include:

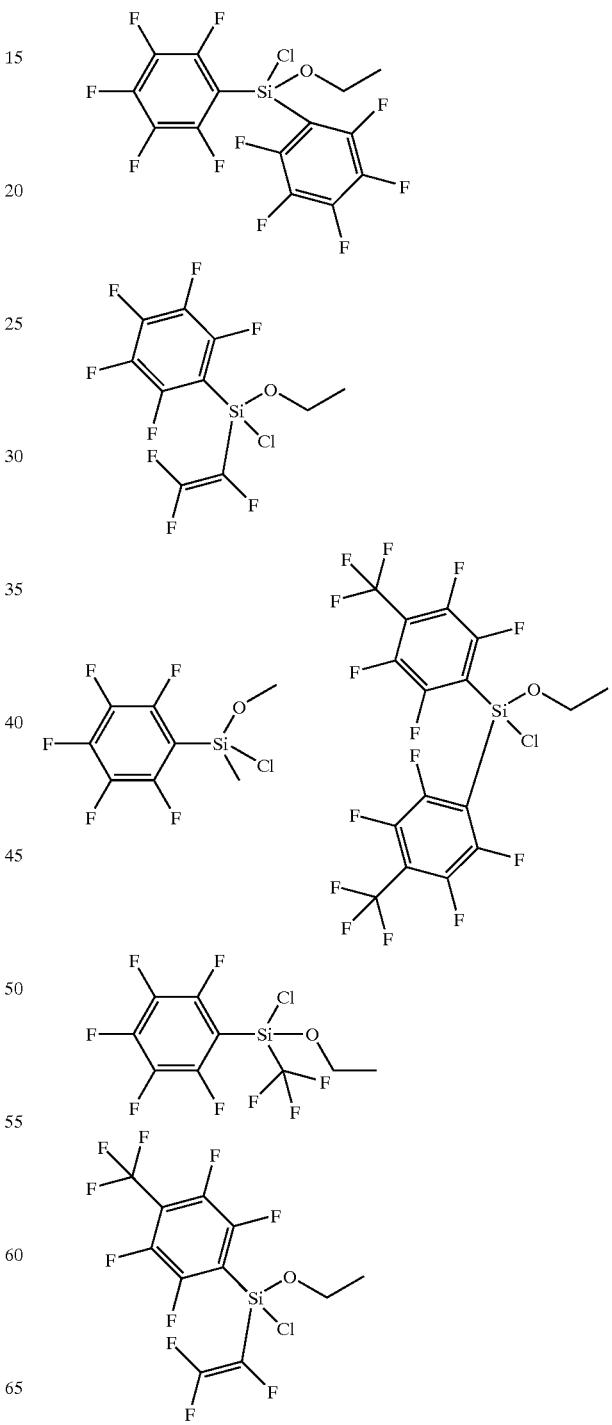

-continued

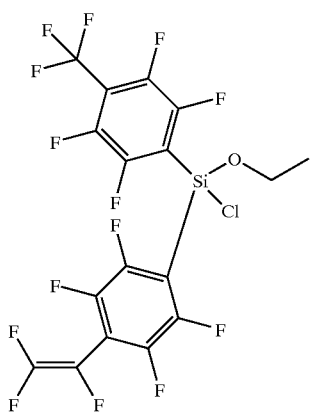

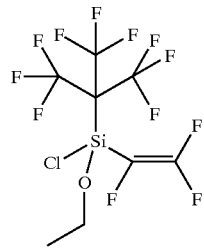

Compound Example VII

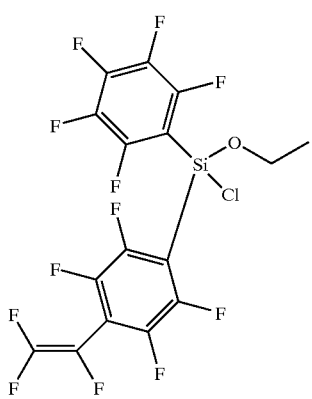

In a further embodiment of the invention, a compound is provided of the general formula: $R^1 R^2 MX_2$, where $R^1$ is any partially or fully fluorinated organic group (preferably a partially or fully fluorinated aryl, alkenyl, alkynyl or alkyl group) as set forth above with respect to $R^1$, $R^2$ is any partially or fully fluorinated organic group (preferably a partially or fully fluorinated aryl, alkenyl, alkynyl or alkyl group) as set forth above with respect to $R^1$, or any such organic groups nonfluorinated, and where $R^1$ and $R^2$ are the same or different from each other, where M is an element selected from group 14 of the periodic table as mentioned above, and where X is a halogen as above—Except where M is Si, $R^1$ and $R^2$ are perfluorinated phenyl, and X is Cl, which, though not novel per se, is novel when used as part of the methods of the invention as will be discussed further below. Specific examples within this category include:

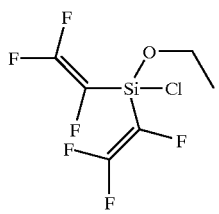

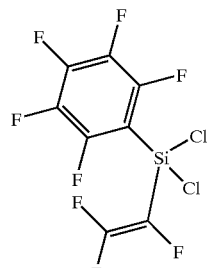 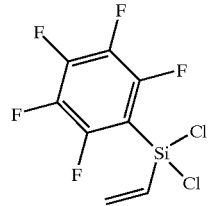

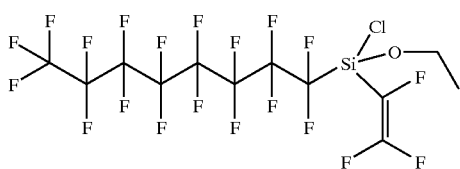

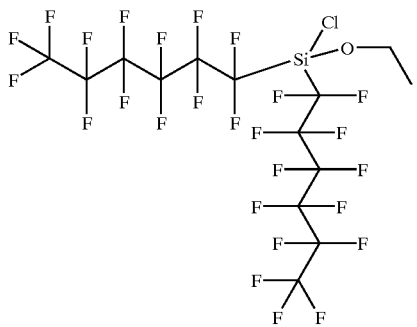

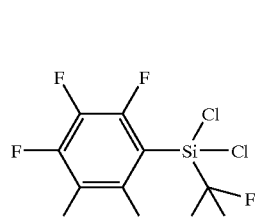 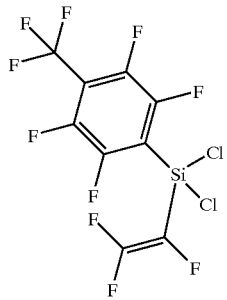

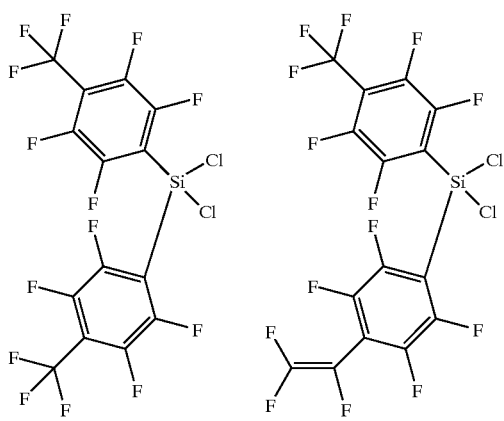

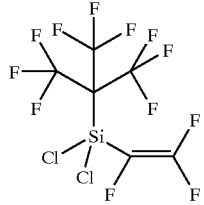

As Compounds V–VII have two organic groups, they can be formed by various combinations of Methods A, B and/or C (described in further detail below).

Compound VIII

In a further embodiment of the invention, a compound is provided of the general formula: $R^1R^2R^3MOR^3$, where $R^1$, $R^2$ and $R^3$ are independently an aryl, alkenyl, alkynyl or alkyl group) as set forth above with respect to $R^1$ and $R^2$, and where $R^1$, $R^2$ and $R^3$ can each be the same or different from each other (and preferably at least one of where $R^1$, $R^2$ and $R^3$ is partially or fully fluorinated), where M is preferably an element selected from group 14 of the periodic table as above, and where $OR^3$ is an alkoxy group as above. One example is

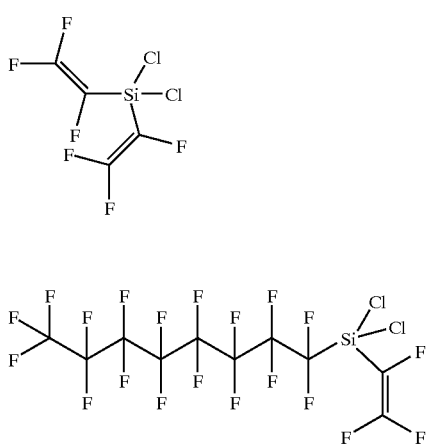

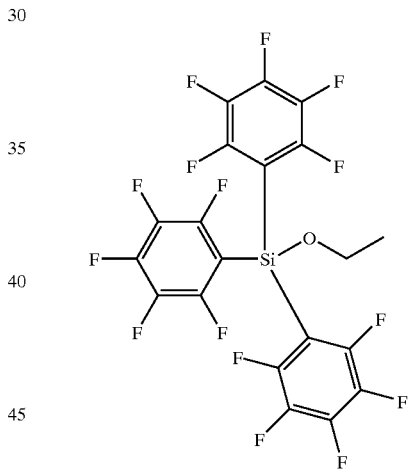

though the organic groups need not each be the same as in this example, and need not each be fluorinated (though preferably at least one of the organic groups is fluorinated).

Compound IX

In another embodiment of the invention, a compound is provided of the general formula: $R^1R^2R^3MX$, where $R^1$, $R^2$ and $R^3$ are independently an aryl, alkenyl, alkynyl or alkyl group) as set forth above with respect to $R^1$ and $R^2$, and where $R^1$, $R^2$ and $R^3$ can each be the same or different from each other (and preferably at least one of where $R^1$, $R^2$ and $R^3$ is partially or fully fluorinated), where M is preferably an element selected from group 14 of the periodic table as above, and where X is a halogen as above. One example is:

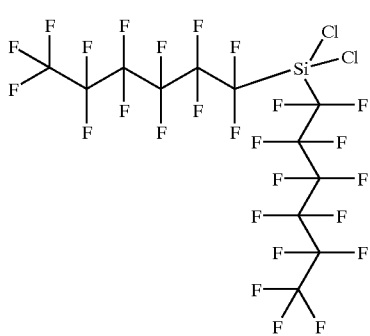

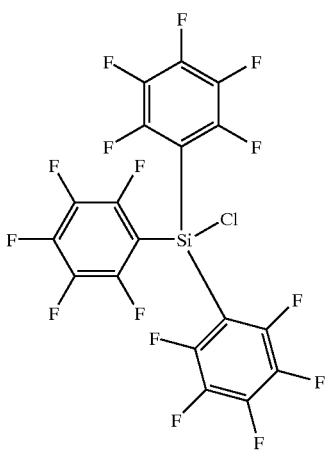

As Compounds VIII and IX have three organic groups, they can be formed by various combinations of Methods A, B and/or C (which methods are described in further detail below).

Other Compounds

Additional compounds within the scope of the invention include those having the general formula $R^1MHX_2$ where $R^1$, M and X are as above and H is hydrogen. One example is:

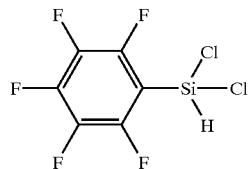

Other examples, where the fluorinated phenyl group is replaced with a substituted phenyl, fluorinated alkyl, vinyl, etc. are possible.

It should be noted that M in the compound formula examples above need not be tetravalent. M can also have other valencies, though preferably tri- or penta-valent. Examples would include early transition metals in group 3 or 5 of the periodic table (e.g. Y, V or Ta), or elements in columns 13 (column headed by B) or 15 (column headed by N), such as B, Al or As. In such situations, the compounds above would have one fewer or one additional alkoxy ($OR^3$), halogen (X) or an organic group ($R^1$ or $R^2$ independently from the other organic group(s)). Examples include $R^1MOR^3X$, $R^1MOR^3{}_2$, $R^1MX_2$, $R^1R^2MX$, $R^1R^2MOR^3$, where M is a trivalent early transition metal (or similar examples with five substituents selected from $R^1$ and/or $R^2$ groups, as well as alkoxy and halogen groups for pentavalent elements (including metalloids or transition metals). Such compounds could have the formula $R1_{3-m}MOR3_m$, $R1_{5-m}MOR3_m$, $R2R1_{4-m}MOR3_m$ or $R2R1_{4-m}MOR3_m$. If such tri- or penta-valent elements are used, such a compound would preferably be hydrolyzed and condensed as a dopant, rather than as the main portion of the material at the time of hydrolysis and condensation (likewise with non-silicon tetravalent elements that form compounds in accordance with the tetravalent examples above, such as germanium compounds).

It should also be noted that the structures illustrated above are exemplary only, as other ring structures (3 sided—e.g. epoxy, or 4 to 8 sided—preferably 5 or 6 sided) are possible, which structures can include nitrogen or oxygen in or bound the ring. The aryl group can have from 1 to 3 substitutents, such as one or more methyl, ethyl, ally, vinyl or other substituents—that can be fluorinated or not. Also, carbon chain R groups can include oxygen (e.g. carboxylate) or nitrogen, or sulpher. If an alkyl group is bound to the silicon (or other M group), it can have from 1 to 4 carbons (e.g. a C2+ straight or C3+ branched chain), or up to 14 carbons (or more)—if used as a bulk enhancing group for later hydrolysis and deposition, 4 or more carbons are preferable. These aryl groups can be fully or partially fluorinated, as can alkenyl or alkynyl groups if used.

Methods of Making the Compounds for Later Hydrolysis and Condensation

In a number of the following examples of methods within the scope of the present invention, "M" is silicon, $OR^3$ is ethoxy, and X is Cl. However, as noted above, other alkoxy groups could easily be used (methoxy, propoxy, etc.), and other group 3–5 or 13–16 elements could be used in place of silicon and other halogens in place of chlorine. Starting materials can vary from tetraethoxy silane, to ethoxy silanes having one or more organic groups bound to the silicon, to chorosilanes having one or more chlorine groups and/or one or more organic groups, as well as starting materials having chlorine and alkoxy groups and with one or more organic groups. Any compound examples within Compounds I–IX above could be used as starting materials—or could be intermediate or final compounds as will be seen below. For example, trifluorovinyltriethoxysilane could be a final compound resulting from reacting a particular trifluorovinyl compound with tetraethoxysilane, or trifluorovinylsilane could be a starting material that, when reacted with a particular pentafluorophenyl compound, results in pentafluorophenyltrifluorovinyldiethoxysilane. As mentioned above, it is also preferred that any organic groups that are part of the starting material or are "added" by chemical reaction to become part of the compound as set forth below, are partially or fully fluorinated (or fully or partially deuterated), though such is not necessary as will also be seen below.

One example of a method of the present invention comprises providing a compound $R^1{}_{4-q}MOR^3{}_q$ where M is selected from group 14 of the periodic table, $OR^3$ is an alkoxy group, $R^1$ is an alkyl, alkenyl, aryl or alkynyl, and q is from 2 to 4; reacting the compound $R^1{}_{4-q}MOR^3{}_q$ with either a) Mg and $R^2X^2$ where $X^2$ is Cl, Br or I and $R^2$ is an alkyl, alkenyl, aryl or alkynyl group, or b) reacting with $R^2X^1$ where $R^2$ is an alkyl, alkenyl, aryl or alkynyl group and wherein $R^2$ is fully or partially fluorinated or deuterated and $X^1$ is an element from group 1 of the periodic table; so as to replace one of the $OR^3$ groups in $R^1{}_{4-q}MOR^3{}_q$ so as to form $R^1{}_{4-q}R^2MOR^3{}_{q-1}$.

The starting material preferably has 1 or 2 (or no) organic groups ($R^1$) bound to the group 14 element "M", which organic groups may or may not comprise fluorine, with the remaining groups bound to M being alkoxy groups. An additional preferably fluorinated (partially of fully) organic group becomes bound to the group 14 element by one of a number of reactions. One method (Method A) involves reacting the starting material with magnesium and a compound having the desired organic group ($R^2$) bound to a halogen $X^2$ (preferably Cl, Br or I)—namely $R^2 X^2$, which reaction replaces one of the alkoxy groups with the organic group $R^2$. In the above example, a single alkoxy group is replaced, however, depending upon the molar ratios of starting material to $R^2X^2$ and Mg, more than one alkoxy group can be replaced with an $R^2$ organic group. In one example of the above, a tetraethoxysilane, $MOR^3_4$ is reacted with a compound $R^2X^2$ where $R^2$ is a preferably fluorinated alkyl, aryl, alkenyl or alkynyl group and $X^2$ is preferably Br or I, so as to form $R^2MOR^3_3$. In another example, $R^1MOR^3_3$ is reacted with $R^2X^2$ so as to form $R^1R^2MOR^3_2$. This group of reactions can be referred to as: reacting the starting material $R^1_{4-q}MOR^3_q$ with $R^2X^2$ where $R^2$ is a preferably fluorinated alkyl, aryl, alkenyl or alkynyl group and $X^2$ is preferably Br or I, so as to form $R^1_{4-q}R^2MOR^3_{q-1}$.

This method A can be described as a method comprising reacting a compound of the general formula $R^1_{4-m}MOR^3_m$, wherein m is an integer from 2 to 4, $OR^3$ is an alkoxy, and M is an element selected from group 14 of the periodic table; with a compound of the general formula $R^2X^2+Mg$, wherein $X^2$ is Br or I, where $R^1$ and $R^2$ are independently selected from alkyl, alkenyl, aryl or alkynyl, and wherein at least one of $R^1$ and $R^2$ is partially or fully fluorinated, so as to make a compound of the general formula $R^2MR^1_{3-n}OR^3_n$, wherein n is an integer from 1 to 3.

An alternate to the above method (Method B) is to react the same starting materials ($R^1_{4-q}MOR^3_q$) with a compound $R^2X^1$ where, as above, $R^2$ is an alkyl, alkenyl, aryl or alkynyl group and wherein $R^2$ is fully or partially fluorinated or deuterated and $X^1$ is an element from group 1 of the periodic table; so as to replace an $OR^3$ group in $R^1_{4-q}MOR^3_q$ to form $R^1_{4-q}R^2MOR^3_{q-1}$. In this example, X1 is an element from group 1 of the periodic table, and is preferably Na, Li or K (more preferably Na or Li). In one example of the above, a tetraethoxysilane, $MOR^3_4$ is reacted with a compound $R^2X^1$ where $R^2$ is a preferably fluorinated alkyl, aryl, alkenyl or alkynyl group and $X^1$ is preferably an element from group I of the periodic table, so as to form $R^2MOR^3_3$. In another example, $R^1MOR^3_3$ is reacted with $R^2X^1$ so as to form $R^1R^2MOR^3_2$.

This method B can be described as a method comprising reacting a compound of the general formula $R1_{4-m}MOR3_m$ wherein m is an integer from 2 to 4, R1 is selected from alkyl, alkenyl, aryl, or alkyl, alkenyl or aryl, and wherein R1 is nonfluorinated, or fully or partially fluorinated, OR3 is alkoxy, and M is an element selected from group 14 of the periodic table; with a compound of the general formula R2M1, wherein R2 is selected from alkyl, alkenyl, aryl, alkynyl, and wherein R2 is at least partially fluorinated; and M1 is an element from group I of the periodic table; so as to make a compound of the general formula $R1_{4-m}MOR3_{m-1}R2$.

A modification (Method C) of the aforementioned (Method B), is to react the starting material ($R^1_{4-q}MOR^3_q$) with a halogen or halogen compound so as to replace one or more of the $OR^3$ groups with a halogen group due to reaction with the halogen or halogen compound. The halogen or halogen compound can be any suitable material such as hydrobromic acid, thionylbromide, hydrochloric acid, chlorine, bromine, thionylchloride or sulfurylchloride and the like. Depending upon the ratio of halogen or halogen compound to starting material (and other parameters such as reaction time and/or temperature), one or more alkoxy groups can be replaced by a halogen group—though in most examples, a single alkoxy group or all alkoxy groups will be replaced. If a single alkoxy group is replaced, then the starting material $R^1_{4-q}MOR^3_q$ becomes $R^1_{4-q}MOR^3_{q-1}X^3$ where $X^3$ is a halogen from the halogen or halogen compound reacted with the starting material (or simply begin with starting material $R^1_{4-q}MOR^3_{q-1}X^3$). If all alkoxy groups are replaced due to the reaction with the halogen or halogen compound, then the starting material $R^1_{4-q}MOR^3_q$ becomes $R^1_{4-q}MX^3_q$. Then, as mentioned for Method B above, either starting material $R^1_{4-q}MOR^3_{q-1}X^3$ or $R^1_{4-q}MX^3_q$ is reacted with a compound $R^2X^1$ where $R^2$ is a preferably fluorinated alkyl, aryl, alkenyl or alkynyl group and $X^1$ is preferably an element from group I of the periodic table, so as to form $R^1_{4-q}R^2MOR^3_{q-1}$, $R^1_{4-q}R^2MX^3_{q-1}$ (or even $R^1_{4-q}R^2_2MX^3_{q-2}$ depending upon reaction conditions). A reaction with $R^1_{4-q}MOR^3_{q-1}X^3$ is preferred due to greater ease of control of the reaction.

This Method C can be described as a method comprising reacting a compound of the general formula $X3MOR3_3$, where X3 is a halogen, M is an element selected from group 14 of the periodic table, and OR3 is alkoxy; with a compound of the general formula R1M1; where R1 is selected from alkyl, alkenyl, aryl and alkynyl and wherein R1 is partially or fully fluorinated; and M1 is an element from group I of the periodic table; so as to form a compound of the general formula $R1MOR3_3$.

Related Methods B and C can be described as a single method comprising reacting a compound of the general formula $R1_{4-m}MOR3_{m-n}X_n$ wherein m is an integer from 2 to 4, and n is an integer from 0 to 2, R1 is selected from alkyl, alkenyl, aryl, or alkyl, alkenyl or aryl, and wherein R1 is nonfluorinated, or fully or partially fluorinated; OR3 is alkoxy, and M is an element selected from group 14 of the periodic table; with a compound of the general formula R2M1, wherein R2 is selected from alkyl, alkenyl, aryl, alkynyl, and wherein R2 is at least partially fluorinated, and M1 is an element from group I of the periodic table; so as to make a compound of the general formula $R2MR1_{4-m}OR3_{m-n}X_{n-1}$.

Of course, as will be seen below, the above starting materials in the method examples set forth above are only examples, as many other starting materials could be used. For example, the starting material could be a halide rather than an alkoxy (e.g. a mono-, di- or trichlorosilanes) or another material having both alkoxy and halogen groups on the group 14 element, along with 0, 1 or even 2 organic groups (alkyl, alkenyl, aryl, alkynyl) also bound to the group 14 element. Though the methods of the invention preferably use starting materials having the group 14 element set forth above, many different combinations of alkoxy groups, halogen groups, and organic groups (alkyl, alkenyl, . . . etc.) can be bound to the group 14 element. And, of course, such starting materials can be commercially available starting materials or can be made from other available starting materials (in which case such materials are intermediate compounds in the methods of the invention).

In addition, the methods of the invention include, it is within the scope of the invention, that a method for forming a final compound could include Methods A, B and/or C above. For example, one organic group, preferably fluorinated, could become bound to the group 14 element M by Method A followed by binding a second organic group, preferably fluorinated, to the group 14 element M by Method B. Or, Method B could be performed first, followed by Method A—or Method C could be performed in combination with Methods A and/or B, etc. And, of course, any particular reaction (binding of an organic group to M) could be performed only once by a particular reaction, or multiple times (binding of multiple organic groups, the same or different from each other) by repeating the same reaction (a, b or c) multiple times. Many combinations of these various reactions and starting materials are possible. Furthermore, any of the methods or method combinations could include any of a number of additional steps including preparation of the starting material, replacing one or more alkoxy groups of the final compound with halogens, purifying the final compound, hydrolysis and condensation of the final compound (as will be described further below), etc.

EXAMPLE 1 (MAKING A COMPOUND I VIA METHOD B)

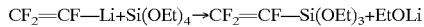

200 ml of freshly distilled dry Et$_2$O is added to a 500 ml vessel (under an argon atmosphere). The vessel is cooled down to −80° C. and 15 g (0.129 mol) of CF$_2$=CFCl gas is bubbled to Et$_2$O. 100 ml (0.13 mol) of sec-BuLi is added dropwise during three hours. The temperature of the solution is kept below −60° C. all the time. The solution is stirred for 15 minutes and 29 ml (27.08 g, 0.130 mol) of Si(OEt)$_4$ is added in small portions. The solution is stirred for over night allowing it to warm up to room temperature. Formed red solution is filtered and evaporated to dryness to result crude trifluorovinyltriethoxysilane, CF$_2$=CFSi(OEt)$_3$.

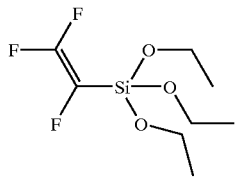

EXAMPLE 2 (MAKING A COMPOUND I VIA METHOD C)

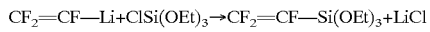

CF$_2$=CFSi(OEt)$_3$ is also formed when 30.80 g (0.155 mol) ClSi(OEt)$_3$ in Et$_2$O is slowly added to solution of CF$_2$=CF—Li (0.155 mol, 13.633 g, prepared in situ) in Et$_2$O at −78° C. Reaction mixture is stirred overnight allowing it slowly warm to room temperature. LiCl is removed by filtration and solution evaporated to dryness to result yellow liquid, crude trifluorovinyltriethoxysilane.

EXAMPLE 3 (making a Compound IV via Method B or C)

Follow steps in Example 1 or 2 above, followed by

24.4 g (0.100 mol) crude trifluorovinyltriethoxysilane, 44 mL (0.60 mol, 71.4 g) thionylchloride and 1.1 g (0.0045 mol) pyridinium hydrochloride are refluxed and stirred for 24 h. Excess of SOCl$_2$ is evaporated and trifluorovinyltriethoxysilane

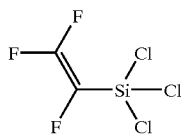

is purified by distillation.

EXAMPLE 4 (MAKING A COMPOUND I VIA METHOD A)

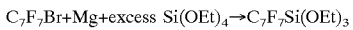

250 g (0.8418 mol) heptafluorobromotoluene, 22.69 g (0.933 mol) magnesium powder, small amount of iodine (15 crystals) and 750 mL (3.3672 mol, 701.49 g) tetraethoxysilane are mixed together at room temperature and diethylether is added dropwise to the vigorously stirred solution until an exothermic reaction is observed (~250 mL). After stirring at room temperature for 16 h diethylether is evaporated. An excess of n-heptane (~600 mL) is added to precipitate the magnesium salts. Solution is filtrated and evaporated to dryness. The residue is fractionally distilled under reduced pressure to yield heptafluorotoluene-triethoxysilane.

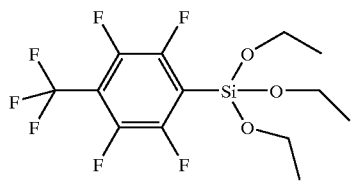

EXAMPLE 5 (MAKING A COMPOUND IV VIA METHOD A)

Follow the steps in Example 4, followed by

2. C$_7$F$_7$Si(OEt)$_3$+6 SOCl$_2$+py.HCl→C$_7$F$_7$SiCl$_3$ where 114.1 g (0.300 mol) heptafluorotoluenetriethoxysilane, 131 mL (1.800 mol, 214.1 g) thionylchloride and 4.51 g (0.039 mol) pyridinium hydrochloride are refluxed and stirred for 16 h. Excess of SOCl$_2$ is evaporated and perfluorotoluenetrichlorosilane

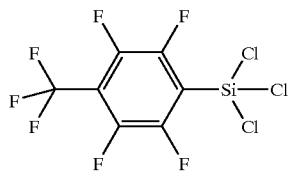

isolated by vacuum-distillation.

EXAMPLE 6 (MAKING A COMPOUND III VIA METHOD A)

Follow same steps as in Example 5, except isolate (by vacuum distillation at the end), perfluorotoluenedichloroethoxysilane, CF$_3$—C$_6$F$_4$—Si(OEt)Cl$_2$

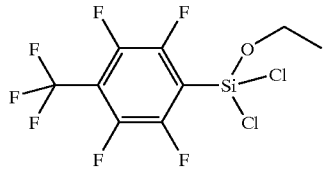

EXAMPLE 7 (MAKING A COMPOUND V FROM A COMPOUND I OR II VIA METHOD C)

1. $C_6F_5Si(OEt)_3 + SOCl_2 + py\cdot HCl \rightarrow C_6F_5Si(OEt)_2Cl + EtCl$
2. $C_6F_5Si(OEt)_2Cl + CF_2=CFLi \rightarrow C_6F_5(CF_2=CF)Si(OEt)_2$
3. $C_6F_5(CF_2=CF)Si(OEt)_2 + \text{excess } SOCl_2 + py\cdot HCl \rightarrow C_6F_5(CF_2=CF)SiCl_2$ 152.0 g (0.460 mol) pentafluorophenyltriethoxysilane, 34 mL (0.460 mol. 54.724 g) thionylchloride and 6.910 g (0.0598 mol) pyridinium hydrochloride are refluxed and stirred for 18 h. Pyridinium hydrochloride is precipitated at −78° C. and the solution is filtrated. Pentafluorophenylchlorodiethoxysilane

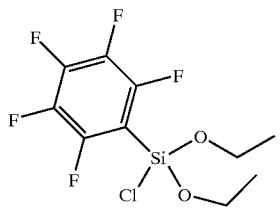

is isolated by vacuum distillation.

Then 49.712 g (0.155 mol) pentafluorophenylchlorodiethoxysilane, $C_6F_5SiCl(OEt)_2$, in $Et_2O$ is slowly added to solution of $CF_2=CF-Li$ (0.155 mol, 13.633 g, prepared in situ) in $Et_2O$ at −78° C. Reaction mixture is stirred overnight while it will slowly warm to room temperature. LiCl is removed by filtration and the product, pentafluorophenyltrifluorovinyldiethoxysilane,

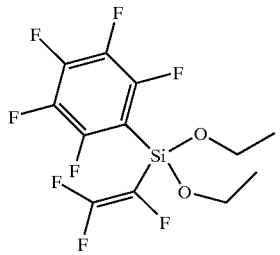

purified by distillation.

EXAMPLE 8 ((MAKING A COMPOUND VII FROM A COMPOUND I OR II VIA METHOD C)

Follow the steps above for Example 7, and then 12.1 g (0.0328 mol) pentafluorophenyltrifluorovinyldiethoxysilane, 12 mL (0.1638 mol 19.487 g) thionylchloride and 0.50 g (0.0043 mol) pyridinium hydrochloride are refluxed and stirred for 24 h. Excess of $SOCl_2$ is evaporated and residue is fractionally distilled under reduced pressure to yield a mixture of 80% pentafluorophenyltrifluorovinyldiethoxysilane.

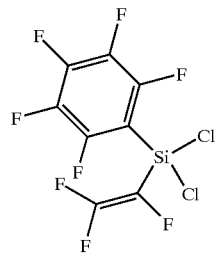

EXAMPLE 9 (MAKING A COMPOUND I VIA METHOD A)

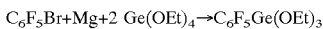

$C_6F_5Br + Mg + 2\ Ge(OEt)_4 \rightarrow C_6F_5Ge(OEt)_3$ 61.5 mL (0.4944 mol, 122.095 g) pentafluorobromobenzene, 13.22 g (0.5438 mol) magnesium powder and 250.00 g (0.9888 mol) tetraethoxygermane are mixed together at room temperature and diethylether is added dropwise to the vigorously stirred solution until an exothermic reaction is observed (400 mL). After stirring at 35° C. for 16 h the mixture is cooled to room temperature and diethylether evaporated. An excess of n-heptane (~400 mL) is added to precipitate the magnesium salts. Solution is filtrated and evaporated to dryness. The residue is fractionally distilled under reduced pressure to yield pentafluorophenyl-triethoxygermane.

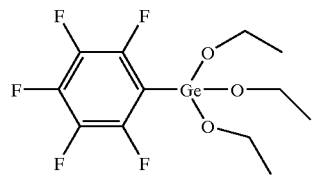

EXAMPLE 10 (MAKING A COMPOUND IV VIA METHOD A)

Follow the steps in Example 9, then:

50 g (0.133 mol) pentafluorophenyltriethoxygermane, 58 mL (0.80 mol, 95.2 g) thionylchloride and 1.97 g (0.017 mol) pyridinium hydrochloride are refluxed and stirred for 24 h. Excess of $SOCl_2$ is evaporated and pentafluorophenyltrichlorogermane isolated by vacuum distillation.

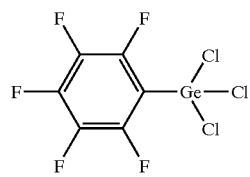

EXAMPLE 11 (MAKING A COMPOUND I VIA METHOD A)

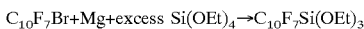

$C_{10}F_7Br + Mg + \text{excess } Si(OEt)_4 \rightarrow C_{10}F_7Si(OEt)_3$ 166.5 g (0.50 mol) 2-bromoperfluoronaphthalene, 13.37 g (0.55 mol) magnesium powder and 448.0 mL (2.00 mol, 416.659 g) tetraethoxysilane are mixed together at room temperature and diethylether is added dropwise to the vigorously stirred solution until an exothermic reaction is observed (~200 mL). After stirring at 35° C. for 16 h the mixture is cooled to room temperature and diethylether evaporated. An excess of n-heptane (~400 mL) is added to precipitate the magnesium salts. Solution is filtrated and evaporated to dryness. The residue is fractionally distilled under reduced pressure to yield perfluoronaphthalenetriethoxysilane.

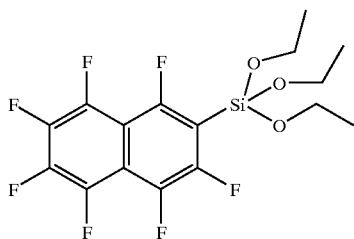

EXAMPLE 12 (MAKING A COMPOUND IV VIA METHOD A)

Follow the steps in Example 11, then 100 g (0.240 mol) perfluoronaphthalenetriethoxysilane, 105.2 mL (1.442 mol, 171.55 g) thionylchloride and 3.54 g (0.0306 mol) pyridinium hydrochloride are refluxed and stirred for 24 h. Excess of SOCl$_2$ is evaporated and perfluoronaphthalenetriethoxysilane isolated by vacuum distillation.

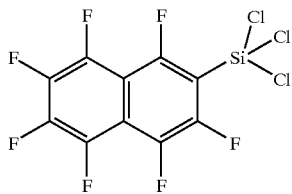

EXAMPLE 13 (MAKING COMPOUND V VIA METHOD A)

C$_6$F$_5$Br+Mg+4 MeSi(OMe)$_3$→C$_6$F$_5$(Me)Si(OMe)$_2$ 57.9 mL (0.465 mol, 114.726 g) bromopentafluorobenzene, 12.42 g (0.511 mol) magnesium powder and 265 mL (1.858 mol, 253.128 g) methyltrimethoxysilane are mixed together at room temperature and diethylether is added dropwise to the vigorously stirred solution until an exothermic reaction is observed (~320 mL). After stirring at 45° C. for 16 h the mixture is cooled to room temperature and diethylether evaporated. An excess of n-heptane (~300 mL) is added to precipitate the magnesium salts. Solution is filtrated and evaporated to dryness. The residue, (methylpentafluorophenyl)dimethoxysilane, is used without further purification.

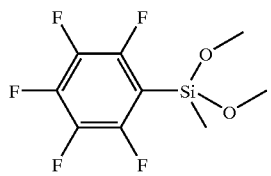

EXAMPLE 14 (MAKING COMPOUND VII VIA METHOD A)

Follow steps in Example 13, then 81.68 g (0.300 mol) methyl(pentafluorophenyl)dimethoxysilane, 109 mL (1.50 mol, 178.4 g) thionylchloride and 3.69 g (0.0319 mol) pyridinium hydrochloride are refluxed and stirred for 16 h. Excess of SOCl$_2$ is evaporated and methyl(pentafluorophenyl)dichlorosilane isolated by vacuum-distillation.

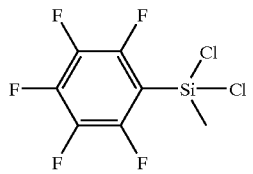

EXAMPLE 15 (MAKING A COMPOUND V VIA METHOD A)

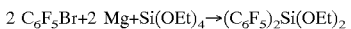

2 C$_6$F$_5$Br+2 Mg+Si(OEt)$_4$→(C$_6$F$_5$)$_2$Si(OEt)$_2$ 265.2 mL (1.95 mol, 525.353 g) bromopentafluorobenzene, 52.11 g (2.144 mol) magnesium powder and 216 mL (0.975 mol, 203.025 g) tetraethoxysilane are mixed together at room temperature and diethylether is added dropwise to the vigorously stirred solution until an exothermic reaction is observed (~240 mL). The solution is stirred for 30 minutes after which additional 90 mL of Et$_2$O is carefully added. After stirring at 35° C. for 16 h the mixture is cooled to room temperature and diethylether evaporated. An excess of n-heptane (~600 mL) is added to precipitate the magnesium salts. Solution is filtrated and evaporated to dryness. The residue is fractionally distilled under reduced pressure to yield di(pentafluorophenyl)diethoxysilane.

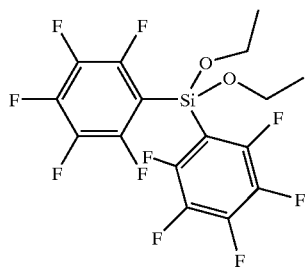

EXAMPLE 16 (MAKING A COMPOUND V VIA METHOD C)

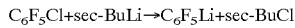

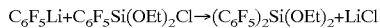

39.52 g (0.195 mol) chloropentafluorobenzene is weighed to a 1000 mL vessel and 250 mL Et$_2$O is added. The vessel is cooled down to −70° C. and 150 mL (0.195 mol) of sec-BuLi (1.3 M) is added dropwise during one hour. The temperature of the solution is kept below −50° C. all the time. The solution is stirred for 30 minutes and 62.54 g (0.195 mol) of diethoxychloropentafluorophenylsilane in Et$_2$O (100 mL) is added in small portions. The solution is stirred for over night allowing it to warm up to room temperature. Formed clear solution is filtered and evaporated to dryness to result di(pentafluorophenyl) diethoxysilane, (C$_6$F$_5$)$_2$Si(OEt)$_2$.

EXAMPLE 17 (MAKING A COMPOUND VII VIA METHOD A or C)

Follow the steps in Example 15 or Example 16, then:

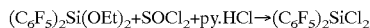

180.93 g (0.400 mol) di(pentafluorophenyl) diethoxysilane, 146 mL (2.00 mol. 237.9 g) thionylchloride and 4.92 g (0.0426 mol) pyridinium hydrochloride are refluxed and stirred for 16 h. Excess of SOCl$_2$ is evaporated and di(pentafluorophenyl)dichlorosilane isolated by vacuum-distillation.

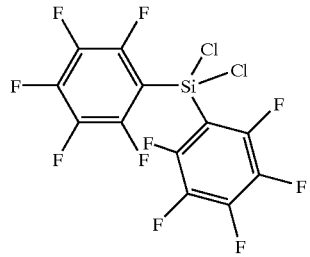

EXAMPLE 18 (MAKING AN "OTHER COMPOUND" VIA METHOD A)

600.0 mL (0.300 mol) pentafluorophenyl magnesiumbromide (0.5 M sol. in Et$_2$O) is added dropwise to a solution of 30.3 mL (0.300 mol, 40.635 g) HSiCl$_3$ in Et$_2$O at −70° C. Reaction mixture is allowed to warm slowly to room temperature by stirring overnight. Diethylether is evaporated and an excess of n-heptane (~200 mL) is added to precipitate the magnesium salts. Solution is filtrated and evaporated to dryness. The residue, pentafluorophenyldichlorosilane, is purified by fractional distillation.

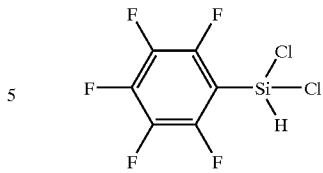

EXAMPLE 19 (MAKING A COMPOUND I VIA METHOD C)

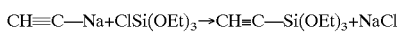

79.49 g (0.400 mol) ClSi(OEt)$_3$ in Et$_2$O is slowly added to a slurry of CH≡C—Na (0.400 mol, 19.208 g) in Xylene/light mineral oil at −78° C. Reaction mixture is stirred overnight allowing it slowly warm to room temperature. NaCl is removed by filtration and solution evaporated to dryness to result acetylenetriethoxysilane.

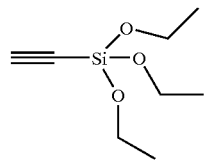

EXAMPLE 20 (MAKING A COMPOUND VII VIA METHOD A)

1. 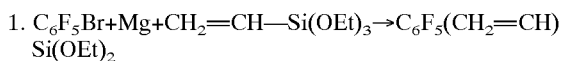
2. 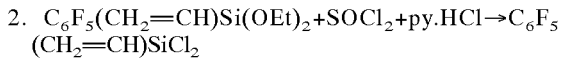

100 mL (0.8021 mol, 198.088 g) pentafluorobromobenzene, 24.90 g (1.024 mol) magnesium powder and 670 mL (3.2084 mol, 610.623 g) vinyltriethoxysilane are mixed together at room temperature and Et$_2$O is added dropwise to the vigorously stirred solution until an exothermic reaction is observed (~400 mL). After stirring at 35° C. for 16 h the mixture is cooled to room temperature and diethylether evaporated. An excess of n-heptane (~500 mL) is added to precipitate the magnesium salts. Solution is filtrated and evaporated to dryness. The residue is fractionally distilled under reduced pressure to yield pentafluorophenylvinyldiethoxysilane.

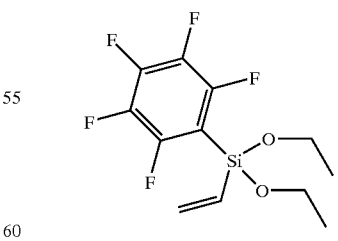

120.275 g (0.3914 mol) pentafluorophenylvinyldiethoxysilane, 143 mL (1.9571 mol, 232.833 g) thionylchloride and 5.880 g (0.0509 mol) pyridinium hydrochloride are refluxed and stirred for 24 h. Excess of SOCl$_2$ is evaporated and pentafluorophenylvinyldiethoxysilane

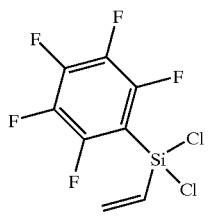

isolated by vacuum distillation.

EXAMPLE 21 (MAKING A COMPOUND I FROM METHOD B)

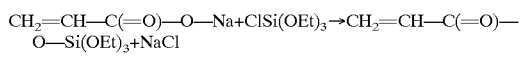

6.123 g (0.0651 mol) sodium acrylate is dissolved to 25 mL THF and cooled to −70° C. 12.8 mL (0.0651 mol, 12.938 g) chlorotriethoxysilane in THF (15 mL) is added dropwise to reaction solution. The solution is stirred for over night allowing it to warm up to room temperature. NaCl is removed by filtration and solution evaporated to dryness to result clear liquid, acryltriethoxysilane.

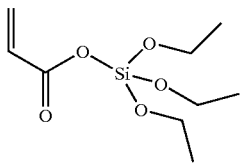

EXAMPLE 22 (MAKING A COMPOUND II)

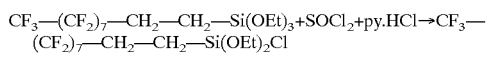

183.11 g (0.300 mol) 1H,1H,2H,2H-Perfluorodecyltriethoxysilane, 22 mL (0.300 mol, 35.69 g) thionylchloride and 4.51 g (0.039 mol) pyridinium hydrochloride are refluxed and stirred for 16 h. Excess of SOCl$_2$ is evaporated and 1H,1H,2H,2H-Perfluorodecylchlorodi(ethoxy)silane isolated by vacuum-distillation.

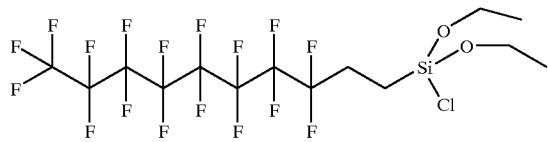

Though this example is not using Methods A, B or C, method C could be used to add a second organic group (replacing the Cl group), or Methods A and B could be used replace an ethoxy group in the starting material with an additional organic group. Also, the starting material could be made by Methods A, B or C (starting earlier with a tetraethoxysilane and reacting as in the other examples herein).

EXAMPLE 23 (MAKING A COMPOUND I VIA METHOD A)

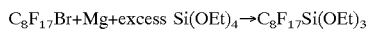

250 g (0.501 mol) 1-Bromoperfluorooctane (or 273.5 g, 0.501 mol 1-Iodoperfluorooctane), 13.39 g (0.551 mol) magnesium powder, small amount of iodine (15 crystals) and 363 mL (2.004 mol, 339.00 g) tetraethoxysilane are mixed together at room temperature and diethylether is added dropwise to the vigorously stirred solution until an exothermic reaction is observed (~200 mL). After stirring at room temperature for 16 h diethylether is evaporated. An excess of n-heptane (~400 mL) is added to precipitate the magnesium salts. Solution is filtrated and evaporated to dryness. The residue is fractionally distilled under reduced pressure to yield perfluorooctyltriethoxysilane.

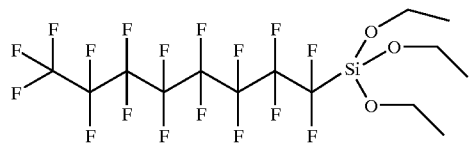

EXAMPLE 24 (MAKING A COMPOUND IV VIA METHOD A)

Follow the steps in Example 23, then 174.7 g (0.300 mol) perfluorooctyltriethoxysilane, 131 mL (1.800 mol, 214.1 g) thionylchloride and 4.51 g (0.039 mol) pyridinium hydrochloride are refluxed and stirred for 16 h. Excess of SOCl$_2$ is evaporated and perfluorooctyltriethoxysilane isolated by vacuum-distillation.

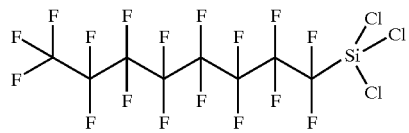

EXAMPLE 25 (MAKING A COMPOUND I VIA METHOD A)

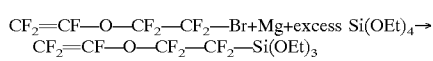

138.47 g (0.500 mol) 2-Bromotetrafluoroethyl trifluorovinyl ether, 13.37 g (0.550 mol) magnesium powder, small amount of iodine (10 crystals) and 362 mL (2.000 mol, 338.33 g) tetraethoxysilane are mixed together at room temperature and diethylether is added dropwise to the vigorously stirred solution until an exothermic reaction is observed (~200 mL). After stirring at room temperature for 16 h diethylether is evaporated. An excess of n-heptane (~400 mL) is added to precipitate the magnesium salts. Solution is filtrated and evaporated to dryness. The residue is fractionally distilled under reduced pressure to yield tetrafluoroethyl trifluorovinyl ether triethoxysilane.

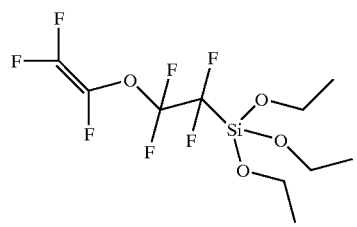

EXAMPLE 26 (MAKING A COMPOUND IV VIA METHOD A)

Follow steps in Example 25, followed by 108.1 g (0.300 mol) tetrafluoroethyl trifluorovinyl ether triethoxysilane, 131 mL (1.800 mol, 214.1 g) thionylchloride and 4.51 g (0.039 mol) pyridinium hydrochloride are refluxed and stirred for 16 h. Excess of SOCl$_2$ is evaporated and tetrafluoroethyl trifluorovinyl ether trichlorosilane is isolated by vacuum-distillation.

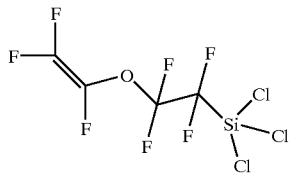

EXAMPLE 27 (MAKING A COMPOUND I VIA METHOD B)

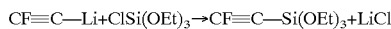

30.80 g (0.155 mol) ClSi(OEt)$_3$ in Et$_2$O is slowly added to solution of CF≡C—Li (0.155 mol, 7.744 g, prepared in situ) in Et$_2$O at −78° C. Reaction mixture is stirred overnight allowing it slowly warm to room temperature. LiCl is removed by filtration and solution evaporated to dryness to result fluoroacetylenetriethoxysilane.

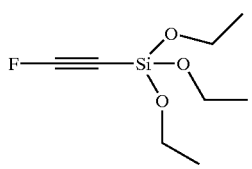

EXAMPLE 28 (MAKING A COMPOUND VIII VIA METHOD C)

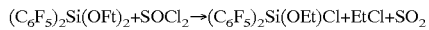

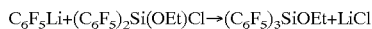

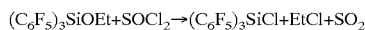

180.93 g (0.400 mol) di(pentafluorophenyl) diethoxysilane, 29 mL (0.400 mol, 47.6 g) thionylchloride and 4.92 g (0.0426 mol) pyridinium hydrochloride are refluxed and stirred for 16 h. Unreacted SOCl$_2$ is evaporated and di(pentafluorophenyl)chloroethoxysilane isolated by vacuum distillation.

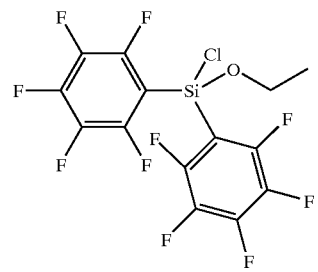

88.54 g (0.200 mol) of di(pentafluorophenyl) chloroethoxysilane in Et$_2$O is slowly added to solution of C$_6$F$_5$—Li (0.200 mol, 34.80 g, prepared in situ) in Et$_2$O at −78° C. The solution is stirred for over night allowing it to warm up to room temperature. Formed clear solution is filtered and evaporated to dryness to result tri (pentafluorophenyl)ethoxysilane, (C$_6$F$_5$)$_3$SiOEt.

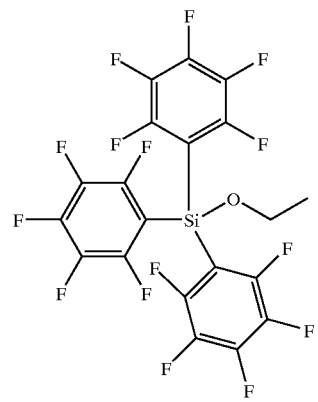

EXAMPLE 29 (MAKING A COMPOUND IX VIA METHOD C)

Follow steps in Example 28, followed by 114.86 g (0.200 mol) tri(pentafluorophenyl)ethoxysilane, 14.6 mL (0.200 mol, 23.8 g) thionylchloride and 2.46 g (0.0213 mol) pyridinium hydrochloride are refluxed and stirred for 16 h. Unreacted SOCl$_2$ is evaporated and tri (pentafluorophenyl)chlorosilane isolated by vacuum-distillation.

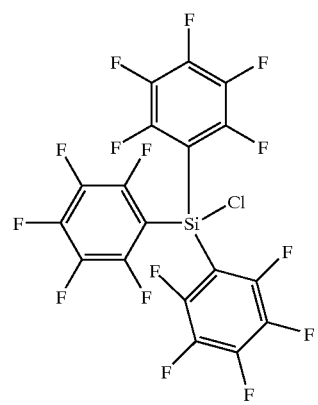

In addition to altering the organic groups in the above examples, it is of course also possible to use other reagents in the methods above. For example, in place of diethyl ether, other solvents such as THF could be used. In place of n-heptane (in Method A) other non polar solvents such as n-hexane could be used. And in place of thionyl chloride (for replacing one or more alkoxy groups with a halogen), chlorine, hydrochloric acid, hydrobromic acid, thionylbromide, chlorine or sulfurylchloride could be used. Also, the temperatures and times (and other process parameters) can be varied as desired. In one embodiment, it is preferred that the molar ratio of the starting material to $R^2X^1$ (Methods B or C) is 0.5:1 to 2:1—preferably 1:1. Also, the starting material and $R^2X^1$ are preferably mixed at a temperature less than −40 C. degrees, e.g. between −50 C and −100 C and warmed to a higher temperature over a period of four hours or more (this higher temperature can be room temperature or higher if desired)—or over a longer period of time such as overnight.

As can be seen from the examples above, Methods B and C of the invention involve reacting a first compound (having an M group selected from group 14 of the periodic table, 0, 1 or 2 organic groups bound to M) with a second compound (having an element from group 1 of the periodic table and a "new" organic group). As can also be seen from the above, such a reaction can take place if the first compound has alkoxy groups bound to M or both alkoxy and halogen groups (0, 1 or 2 halogen groups) bound to M. Method C, as mentioned earlier, is a variation of Method B—and both methods can be viewed as comprising: reacting a compound of the general formula $R^1_{4-m}MOR^3_{m-n}X_n$, where $R^1$ is any nonfluorinated (including deuterated) or partially or fully fluorinated organic group (preferably a partially or fully fluorinated aryl, alkenyl, alkynyl or alkyl group) as set forth above, where M is selected from group 14 of the periodic table, where X is a halogen, where $OR^3$ is an alkoxy group, where m=2 to 4 and n=0 to 2. $R^1_{4-m}MOR^3_{m-n}X_n$ is reacted with $R^2X^1$ where $R^2$ is selected from alkyl, alkenyl, aryl or alkynyl (and where $R^2$ is fluorinated (fully or partially), and where $X^1$ is an element from group 1 of the periodic table. $X^1$ is preferably Na, Li or K, more preferably Na or Li, and most preferably Li. M is preferably Si, Ge or Sn, more preferably Si or Ge, and most preferably Si. X is preferably Cl, Br or I, more preferably Cl or Br, and most preferably CL $OR^3$ is preferably an alkoxy group having from 1 to 4 carbon atoms, more preferably from 1 to 3 carbons, and most preferably 2 carbons (ethoxy). Also, "m" is preferably 3 or 4, whereas "n" is preferably 0 or 1.

$R^1$ and $R^2$ are independently preferably partially or fully fluorinated (though not necessarily as can be seen in prior examples) organic groups such as an aryl group (by aryl group we mean any organic group having a ring structure) though preferably a five or six carbon ring that is unsubstituted or substituted. For a six carbon ring structure, 1, 2 or 3 substituents can be bound to the ring, which substituents can be actively bound to the ring via a variation on the Method C set forth above (to be described further below). The substituents can be alkyl groups of any desired length, straight or branched chain, preferably fluorinated, and preferably having from 1 to 4 carbon atoms. Or the substituents on the ring structure can comprise a C=C double bond and be an alkenyl group (by alkenyl group we mean any organic group with a C=C double bond) such as an acrylate, vinyl or allyl group. A fluorinated vinyl, methyl or ethyl group on a fluorinated phenyl group are examples. Or, the aryl group could be a multi ring structure (e.g. perfluoronaphthalene or a biphenyl group). Or $R^1$ and $R^2$ could independently be an alkenyl group such as a vinyl or longer chain group having a C=C double bond, or a group having other types of double bonds (e.g C=O double bonds or both C=C and C=O double bonds) such as acrylate and methacrylate groups. $R^1$ and $R^2$ could also be an alkynyl group (by alkynyl group we mean any organic group with a carbon-carbon triple bond) as mentioned previously, as well as an alkyl group. If an alkyl group (by alkyl group we mean a carbon chain of any length), preferably the carbon chain is from 1 to 14, and more preferably from 4 to 8. Perfluorinated alkyl groups from 1 to 8 carbons can be used, as well as fluorinated (e.g. partially fluorinated) groups longer than 8 carbons. All the organic groups above could be deuterated in stead of fluorinated (or partially deuterated and partially fluorinated), though fully or partially fluorinated (particularly fully fluorinated) is preferred.

In Method C set forth above, an organic (or hybrid) group "R" (e.g. R2) becomes bound to a group 3–6 or 13–16 element "M" by replacing a halogen "X" bound to "M" via the specified reaction. In an alternative to this method (Method D), an organic (or hybrid) group "R" (e.g. R1) comprises the halogen "X"—preferably Cl or Br (rather than "X" being bound to "M"). Thus when the reaction is performed, R2 replaces X bound to R1, such that R2 becomes bound to R1 (which is in turn bound to M). Preferably the other groups bound to M are alkoxy groups (OR3) or other organic groups. More particularly, such a method comprises providing a compound $X_aR^1MOR^3_2R^4$ where a is from 1 to 3, X is a halogen(s) bound to $R^1$, R1 is an organic group (preferably an aryl, alkyl, alkenyl or alkynyl—more preferably an alkyl or aryl group), $OR^3$ is an alkoxy, and $R^4$ is either an additional alkoxy group or an additional organic group (selected from aryl, alkyl, alkenyl or alkynyl), and reacting this compound with $R^2M^1$ where $M^1$ is selected from group 1 of the periodic table and $R^2$ is an organic group preferably selected from aryl, alkyl, alkenyl and alkynyl, etc., so as to form $R^2_aR^1MOR^3_2R^4$.

In one embodiment, $R^4$ is an alkoxy group the same as $OR^3$, such that the method comprises reacting $X_aR^1MOR^3_3$ with $R^2M^1$ to form $R^2_aR^1MOR^3_3$ (where $R^1$ and $OR^3$ are bound to M and $R^2$ is bound to $R^1$. In another embodiment, $R^4$ is an organic group selected from aryl, alkyl, alkenyl and alkynyl. Preferably $OR^3$ is a methoxy, ethoxy or propoxy, $R^1$ is an aryl or alkyl (straight or branched chain) having from 1 to 14 carbons, and $R^2$ is an aryl, alkyl, alkenyl or alkynyl, where a=1 or 2 if $R^1$ is an alkyl and a=1, 2 or 3 if $R^1$ is an aryl group. $R^2$ can be an epoxy, acrylate, methacrylate, vinyl, allyl or other group capable of cross linking when exposed to an electron beam or in the presence of a photoinitiator and electromagnetic energy (e.g. UV light).

EXAMPLE A (FORMING A COMPOUND I OR IV VIA METHOD D)

1. $1,4-Br_2C_6F_4 + Mg + Si(OEt)_4 \longrightarrow Br(C_6F_4)Si(OEt)_3$

2. $Br(C_6F_4)Si(OEt)_3 + CF_2=CFLi \longrightarrow (CF_2=CF)(C_6F_4)Si(OEt)_3$

3. $(CF_2=CF)(C_6F_4)Si(OEt)_3 + \text{excess } SOCl_2 \xrightarrow{\text{py·HCl}} (CF_2=CF)(C_6F_4)SiCl_3$ 250 g (0.812 mol) 1,4-dibromotetrafluorobenzene, 21.709 g (0.8932 mol) magnesium powder, small amount of iodine (15 crystals) and 181 mL (0.812 mol, 169.164 g) tetraethoxysilane were mixed together at room temperature and diethylether was added dropwise to the vigorously stirred solution until an exothermic reaction was observed (~250 mL). After stirring at room temperature for 16 h diethylether was evaporated. An excess of n-heptane (~600 mL) was added to precipitate the magnesium salts. Solution was filtrated and evaporated to dryness. The residue was fractionally distilled under reduced pressure to yield 4-bromotetrafluorophenyltriethoxysilane.

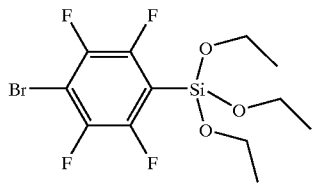

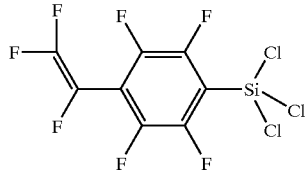

The above example could be modified where 2 or 3 halogens (in this case Br) are bound to the phenyl group so as to result in multiple vinyl substituents. Also, the phenyl group could be another organic group such as an straight or branched chain alkyl group, a multi ring aryl group, etc., whereas the vinyl group could be any suitable organic group capable of binding to a group I element (in the above example Li) and replacing the halogen (in the above example Br). Examples other than vinyl include methyl, ethyl, propyl, phenyl, epoxy and acrylate.

EXAMPLE B (FORMING A COMPOUND I VIA METHOD D)

$CF_2Cl-C(=O)-ONa + ClSi(OEt)_3 \rightarrow CF_2Cl-C(=O)-O-Si(OEt)_3 + NaCl$ $CF_2=CF-Li + CF_2Cl-C(=O)-O-Si(OEt)_3 \rightarrow CF_2=CF-CF_2-C(=O)-O-Si(OEt)_3 + LiCl$ 78.246 g (0.200 mol) 4-bromotetrafluorophenyltriethoxysilane in $Et_2O$ is slowly added to solution of $CF_2=CF-Li$ (0.200 mol, 17.592 g, prepared in situ) in $Et_2O$ at $-78°$ C. Reaction mixture is stirred overnight while it will slowly warm to room temperate. LiBr is removed by filtration and the product, 4-triethoxysilyl-perfluorostyrene, purified by distillation.

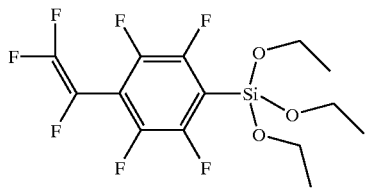

117.704 g (0.300 mol) 4-triethoxysilylperfluorostyrene, 131 mL (1.800 mol, 214.1 g) thionylchloride and 4.51 g (0.039 mol) pyridinium hydrochloride were refluxed and stirred for 16 h. Excess of $SOCl_2$ was evaporated and 4-trichlorosilyl-perfluorostyrene isolated by vacuum-distillation.

15.246 g (0.10 mol) sodium chlorodifluoroacetate, is dissolved to 100 mL $Et_2O$ and cooled to $-70°$ C. 19.7 mL (0.10 mol, 19.872 g) chlorotriethoxysilane in $Et_2O$ (50 mL) was added dropwise to reaction solution. The solution was stirred for over night allowing it to warm up to room temperature. NaCl is removed by filtration and solution evaporated to dryness to result clear colourless liquid, chlorodifluoroacetic acid, triethoxysilyl ester.

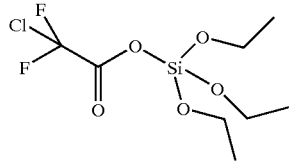

29.27 g (0.10 mol) chlorodifluoroacetic acid, triethoxysilyl ester, is dissolved to 100 mL $Et_2O$ and slowly added to solution of $CF_2=CF-Li$ (0.10 mol, 8.796 g, prepared in situ) in $Et_2O$ at $-78°$ C. Reaction mixture is stirred overnight allowing it slowly warm to room temperature. LiCl is removed by filtration and solution evaporated to dryness to result yellow liquid, crude perfluoro-3-butene acid, triethoxysilyl ester.

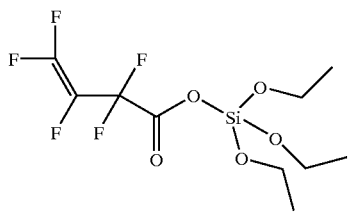

EXAMPLE C (FORMING A COMPOUND I OR IV VIA METHOD D)

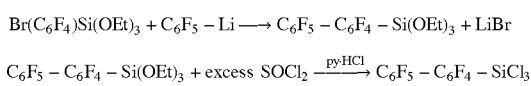

78.246 g (0.200 mol) 4-bromotetrafluorophenyltriethoxysilane in Et$_2$O is slowly added to solution of C$_6$F$_5$—Li (0.200 mol, 34.80 g, prepared in situ) in Et$_2$O at −78° C. Reaction mixture is stirred overnight while it will slowly warm to room temperature. LiBr is removed by filtration and the product, perfluorobiphenyltriethoxysilane, purified by distillation.

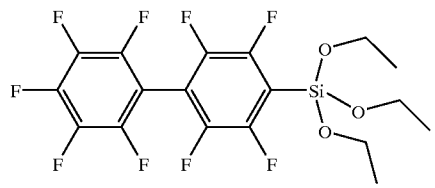

143.516 g (0.300 mol) perfluorobiphenyltriethoxysilane, 131 mL (1.800 mol, 214.1 g) thionylchloride and 4.51 g (0.039 mol) pyridinium hydrochloride were refluxed and stirred for 16 h. Excess of SOCl$_2$ was evaporated and perfluorobiphenyltrichlorosilane isolated by vacuum-distillation.

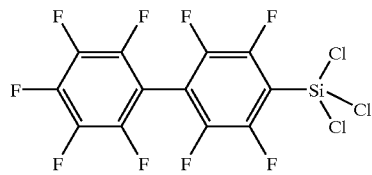

EXAMPLE D (FORMING A COMPOUND I OR IV VIA METHOD D)

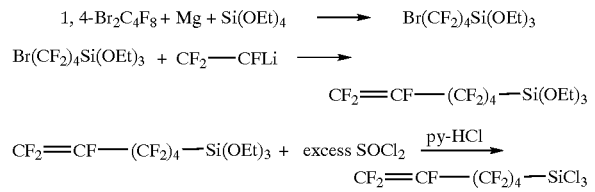

143.94 g (0.40 mol) 1,4-dibromooctafluorobutane, 10.69 g (0.44 mol) magnesium powder, small amount of iodine (15 crystals) and 88 mL (0.40 mol, 82.42 g) tetraethoxysilane were mixed together at room temperature and diethylether was added dropwise to the vigorously stirred solution until an exothermic reaction was observed (~200 mL). After stirring at room temperature for 16 h diethylether was evaporated. An excess of n-heptane (~400 mL) was added to precipitate the magnesium salts. Solution was filtrated and evaporated to dryness. The residue was fractionally distilled under reduced pressure to yield 4-bromooctafluorobutanetriethoxysilane.

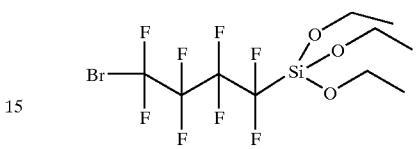

88.641 g (0.200 mol) 4-bromooctafluorobutanetriethoxysilane in Et$_2$O is slowly added to solution of CF$_2$=CF—Li (0.200 mol, 17.592 g, prepared in situ) in Et$_2$O at −78° C. Reaction mixture is stirred overnight while it will slowly warm to room temperature. LiBr is removed by filtration and the product, perfluoro-1-hexenetriethoxysilane, purified by distillation.

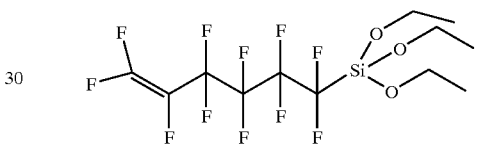

133.295 g (0.300 mol) perfluoro-1-hexenetriethoxysilane, 131 mL (1.800 mol, 214.1 g) thionylchloride and 4.51 g (0.039 mol) pyridinium hydrochloride were refluxed and stirred for 16 h. Excess of SOCl$_2$ was evaporated and perfluoro-1-hexenetrichlorosilane isolated by vacuum-distillation.

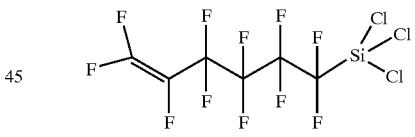

In the above "Method D" examples, $R^1$, $R^2$, $R^3$ and $R^4$ are preferably partially or fully fluorinated.

Hydrolysis and Condensation of the Compound(s)

Compounds IV, VII and IX have organic (or hybrid) R group(s) and halogen(s) (preferably Br or Cl) bound to M (selected from groups 3–6 or 13–16—preferably group 14)). These compounds can be hydrolyzed alone or in any combination to result in a material having a —M—O—M—O— backbone with R groups bound to the backbone, and that preferably has a molecular weight of from 500 to 10,000 (more preferably from 1000 to 5000). In one embodiment, a compound selected from Compound IV is hydrolyzed with another compound selected from Compound IV. In another embodiment, a single compound from Compound VII is hydrolyzed. Many other combinations are possible, including: a) Compound IV+Compound VII; b) Compound IV+Compound IV+Compound IV; c) Compound VII+

Compound VII; d) Compound IV+Compound VII+Compound IX; e) Compound IV+Compound IV+Compound IX; f) Compound VII+Compound IX, etc. Any other combinations, in any desired ratio, can be used for the hydrolysis and eventual deposition.

HYDROLYSIS EXAMPLE 1—COMPOUND IV+COMPOUND IV

If one of the compounds to be hydrolyzed and condensed is pentafluorophenyltrichlorosilane, this can be prepared as in the methods set forth above, by:

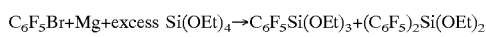

C$_6$F$_5$Br+Mg+excess Si(OEt)$_4$→C$_6$F$_5$Si(OEt)$_3$+(C$_6$F$_5$)$_2$Si(OEt)$_2$

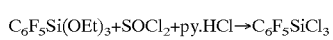

C$_6$F$_5$Si(OEt)$_3$+SOCl$_2$+py.HCl→C$_6$F$_5$SiCl$_3$ 100 mL (0.8021 mol, 198.088 g) pentafluorobromobenzene, 24.90 g (1.024 mol) magnesium powder and 716 mL (3.2084 mol, 668.403 g) tetraethoxysilane are mixed together at room temperature and diethylether is added dropwise to the vigorously stirred solution until an exothermic reaction is observed (~200 mL). After stirring at 35° C. for 16 h the mixture is cooled to room temperature and diethylether evaporated. An excess of n-heptane (~500 mL) is added to precipitate the magnesium salts. Solution is filtrated and evaporated to dryness. The residue is fractionally distilled under reduced pressure to yield pentafluorophenyltriethoxysilane.

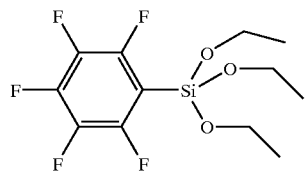

100 mL (0.375 mol, 124.0 g) pentafluorophenyltriethoxysilane, 167 mL (2.29 mol, 272.0 g) thionylchloride and 5.63 g (0.0487 mol) pyridinium hydrochloride are refluxed and stirred for 24 h. Excess of SOCl$_2$ is evaporated and pentafluorophenyltrichlorosilane

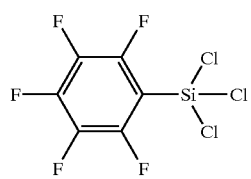

isolated by vacuum-distillation.

If a second of the compounds to be hydrolyzed and condensed is trifluorovinyltriethoxysilane, this can be prepared by:

119 mL (0.155 mol) sec-butyllithium (1.3 M solution in cyclohexane) is added under argon with stirring to 18.053 g (0.155 mol) chlorotrifluoroethylene

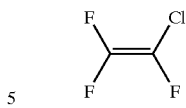

dissolved in Et$_2$O at −80° C. After the addition is complete the reaction mixture is stirred for 15 min to yield lithiumtrifluoroethylene.

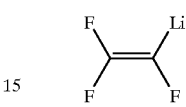

30.80 g (0.155 mol) ClSi(OEt)$_3$ in Et$_2$O is slowly added to solution of CF$_2$=CF—Li (0.155 mol, 13.633 g, prepared in situ) in Et$_2$O at −78° C. Reaction mixture is stirred overnight while it will slowly warm to room temperature. LiCl is removed by filtration and the product, trifluorovinyltriethoxysilane,

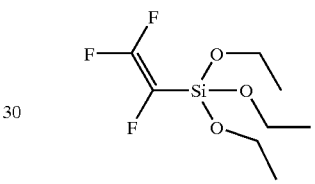

is isolated by distillation.

24.4 g (0.100 mol) trifluorovinyltriethoxysilane, 44 mL (0.60 mol, 71.4 g) thionylchloride and 0.497 g (0.0045 mol) pyridinium hydrochloride are refluxed and stirred for 24 h. Excess of SOCl$_2$ is evaporated and trifluorovinyltrichlorosilane

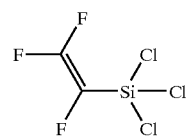

is purified by distillation.

Then, to a solution of trifluorovinyltrichlorosilane and pentafluorophenyltrichlorosilane at a molar ratio 1:1 in dehydrated tetrahydrofuran, is added dropwise a stoichiometric amount of water (e.g. H20 or D2O) in THF at 0° C. (nonstoichiometric amounts, higher or lower, can also be used). After stirring for 1 hour, the solution is neutralized with 3 equivalents of sodium hydrogencarbonate. After confirming the completion of generation of carbonic acid gas from the reaction solution, the solution is filtered and volatile compounds are removed by vacuum evaporation to obtain colorless, transparent viscous fluid, poly (pentafluorophenyltrifluorovinylsiloxane), in a three dimensional network of alternating silicon and oxygen atoms.

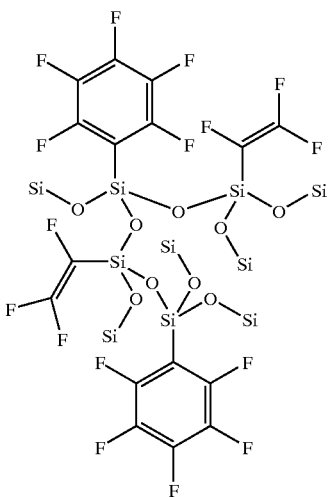

The above is but one example of a method comprising: reacting a compound of the general formula R1MX3₃ with a compound of the general formula R2MX3₃ where R1 is selected from alkyl, alkenyl, aryl and alkynyl, R2 is selected from alkenyl, aryl or alkynyl, M is an element selected from groups 3–6 or 13–16 though preferably from group 14 of the periodic table, and X3 is a halogen; with H2O or D2O; so as to form a compound having a molecular weight of from 500 to 10,000 with a —M—O—M—O— backbone with R1 and R2 substituents on each M.

In the hydrolysis example above, silicon atoms of the network are modified by pentafluorophenyl and trifluorovinyl groups in an approximate ratio 1:1. Of course other ratios are possible depending upon the ratio of starting materials, and, of course, other three dimensional networks can be achieved by having other (or additional) starting materials selected from Compound IV, VII and IX, along with other hydrolyzable materials. An alternate example is a method comprising: reacting a compound of the general formula R1R2MX3₂ where R1 is selected from alkyl, alkenyl, aryl and alkynyl, R2 is selected from alkenyl, aryl or alkynyl, M is an element selected from group 14 of the periodic table, and X3 is a halogen; with D2O; so as to form a compound having a molecular weight of from 500 to 10,000 with a —M—O—M—O— backbone with R1 and R2 substituents on each M.

Also, though "M" in the above hydrolysis example is silicon, it is possible to have materials with other M groups, or "dope" one or more silanes to be hydrolyzed with a lesser amount of a compound having a different M group such as germanium (or boron, aluminum, selenium, etc.).

Deposition of the Hydrolyzed and Condensed Material

The material formed as above preferably has a molecular weight between 500 and 10,000, more preferably between 1000 and 5000. Other molecular weights are possible within the scope of the invention, however a weight between 1000 and 5000 provides the best properties for depositing the material on a substrate. The substrate can be any suitable substrate, such as any article of manufacture that could benefit from a hydrophobic and/or transparent layer or coating. In the fields of electronics and optical communications, the material could be deposited as a final passivation layer, as a glob top coating, as an underfill in a flip chip process, as a hermetic packaging layer, etc. Because the material can be patterned as will be discussed further below, the material could be deposited on a substrate (e.g. a glass, quartz, silicon or other wafer) as a buffer/cladding, waveguide/core or other layer within a waveguide or other optoelectronic/photonic device.

In general, the siloxane oligomer having the molecular weight as set forth above is mixed with a suitable solvent and deposited. If the material is to be patterned by exposure to electromagnetic radiation (e.g. UV light) then a photoinitiator can be mixed into the material along with the solvent. There are many suitable types of photoinitiators that could be used, such as Irgacure 184, Irgacure 500, Irgacure 784, Irgacure 819, Irgacure 1300, Irgacure 1800, Darocure 1173 or Darocure 4265. The initiator could be highly fluorinated, such as 1,4-bis(pentafluorobenzoyl)benzene or Rhodosil 2074 photoinitiator. Also, thermal initiators can be applied for thermal crosslinking of organic carbon double bond moieties, such as with Benzoyl peroxide, 2,2'-Azobisisobutyronitrile, or tert-Butyl hydroperoxide.

DEPOSITION EXAMPLE 1

Add 10 w-% of methyl isobutyl ketone and 2 w-% of Irgacure 819 photoinitiator to result in the formation of a spin-coatable and photo-sensitive material. The material is deposited by spin coating, spray coating, dip coating, etc. onto a substrate or other article of manufacture. As mentioned herein, many other organic groups can be used in place of the above groups, though preferably one of the groups in one of the compounds is capable of cross linking when exposed to electromagnetic energy (or an electron beam)—e.g. an organic group with a ring structure (e.g. an epoxy) or a double bond (e.g. vinyl, allyl, acrylate, etc.).

Forming a Waveguide

One use of the material set forth above is as a layer within a waveguide. Though the waveguide could be a fiber optic waveguide (with substantially circular cross section) the example below is in relation to a planar waveguide. On a substrate (PCB, IC, silicon, glass or quartz wafer, etc.) is deposited a lower cladding layer. (A buffer layer can first be deposited if desired.) The cladding layer is made by forming Compounds IV, VII and/or IX and hydrolyzing such compound(s), followed by mixing the hydrolyzed material with a solvent and thermal initiator and then depositing onto the substrate. After deposition, the cladding layer can be fully or partially baked (or exposed to UV light if a photoinitiator is used in place of the thermal initiator) to solidify the cladding. On the cladding layer is deposited a core layer that is made and deposited as above, except with a different ratio of compounds or different compounds that are hydrolyzed/condensed to form the material ready for deposition. By modifying the hydrolysable compounds and/or ratios of compounds in the core layer vs. those in the cladding layer, a different index of refraction is achieved. A developer (e.g. e.g. methanol ethanol, propanol, acetone, methyl isobutyl ketone, tetrahydrofuran, Dow Chemical DS2100, Dow Chemical DS3000, etc.) is then applied to remove unexposed material. In this way, a core for the waveguide is formed. Then an upper cladding layer is made and deposited in the same way as the lower cladding layer. Though in this example the mask is a binary mask (the material is either fully exposed or not exposed to electromagnetic radiation), it is also possible to provide partial exposure (e.g. in a continuum from full exposure to a low or non-exposure level as in a gray scale mask). Such a gray scale exposure can form a vertical taper in the waveguide when the developer is applied.

This invention has been described in connection with the preferred embodiments. Many variations of the above embodiments are contemplated as being within the scope of the invention.

What is claimed is:

1. A method comprising:

reacting a compound of the general formula (I)

$$R1_{4-m}MOR3_{m-n}X_n$$

wherein m is an integer from 2 to 4, and n is an integer from 0 to 3 and is not greater than m;

R1 is selected from alkyl, alkenyl, aryl, alkynyl or epoxy, and wherein R1 is nonfluorinated, or fully or partially fluorinated;

OR3 is alkoxy;

X is a halogen; and

M is an element selected from group 14 of the periodic table;

with a compound of the general formula $$R2M1$$

wherein R2 is selected from alkyl, alkenyl, aryl, alkynyl or epoxy, and wherein R2 is at least partially fluorinated; and M1 is an element from group I of the periodic table;

so as to make a compound of the general formula $$R2MR1_{4-m}OR3_{m-n}X_{n-1} \text{ if } n>0 \text{ or } R2MR1_{4-m}OR3_{m-1} \text{ if } n=0.$$

2. The method of claim 1, wherein M1 is Na, Li or K.

3. The method of claim 1, wherein R2 is fully or partially fluorinated.

4. The method of claim 3, wherein R2 is a fully or partially fluorinated alkenyl or alkynyl group.

5. The method of claim 1, wherein R2 is an alkyl group having from 1 to 14 carbons, vinyl or allyl group.

6. The method of claim 1, wherein R2 is a fully or partially fluorinated alkenyl group.

7. The method of claim 1, wherein R1 is a fully or partially fluorinated or nonfluorinated alkenyl group.

8. The method of claim 1, wherein R1 is an aryl group having one or more rings, or an alkyl group having from 1 to 14 carbons.

9. The method of claim 8, wherein the aryl group or alkyl group of R1 is fully or partially fluorinated.

10. The method of claim 9, wherein the aryl group or alkyl group of R1 is fully fluorinated.

11. The method of claim 10, wherein R1 is a fully or partially fluorinated phenyl or fluorinated alkyl group having from 4 to 10 carbon atoms.

12. The method of claim 11, wherein the fully or partially fluorinated phenyl group of R1 is substituted with fully or partially fluorinated methyl, vinyl or ethyl groups.

13. The method of claim 1, wherein OR3 is C1–C4 alkoxy.

14. The method of claim 1, wherein M is Si, Ge, Al or Sn.

15. The method of claim 1, further comprising:

a) reacting a compound of the general formula:

$$R5_{4-m}M2R6_m$$

wherein m is an integer from 2 to 4,

R5 is selected from alkyl, alkenyl, aryl, or fluorinated alkyl, alkenyl or aryl;

R6 is alkoxy; and

M2 is an element selected from groups 3–6 or 13–16 of the periodic table;

with a compound of the general formula:

$$R7M3$$

wherein R7 is selected from alkyl, alkenyl, aryl, alkynyl, and wherein R7 is at least partially fluorinated; and M3 is an element from group I of the periodic table;

so as to make a compound of the general formula:

$$R7M2R5_{3-n}R6_n,$$

wherein n is an integer from 1 to 3.

16. The method of claim 15, wherein M is Si, and M2 is an element selected from groups 14–16 of the periodic table other than Si.

17. The method of claim 15, wherein at least one of R2, R1, R7 and R5 comprises an alkenyl group and wherein $R2MR1_{3-n}OR3_n$ and $R7M2R5_{3-n}R6_n$ are hydrolyzed and condensed together so as to undergo cross linking.

18. The method of claim 1, wherein OR3 is C1–C3 alkoxy.

19. The method of claim 1, wherein R2 is a C2+ straight chain or C3+ branched chain.

20. The method of claim 1, wherein n is 1.

21. The method of claim 20, wherein n is 2.

22. The method of claim 1, wherein m is 2 or 3.

23. The method of claim 22, wherein M is Si.

24. The method of claim 2, wherein M1 is Na or Li.

25. The method of claim 1, wherein n is 1 such that $R2MR1_{4-m}OR3_{m-1}$ is made and further comprising reacting the compound of the general formula $R2MR1_{4-m}OR3_{m-1}$ with a halogen or halide compound so as to form a compound of the general formula $R2MR1_{4-m}X3_{m-1}$ where X3 is a halogen.

26. The method of claim 25, wherein m is 3.

27. The method of claim 1, wherein X is Br or Cl.

28. The method of claim 27, wherein n is from 1 to 3.

29. The method of claim 25, wherein the halogen or halide compound is hydrobromic acid, thionylbromide, hydrochloric acid, chlorine, thionylchloride or sulfurylchloride.

30. The method of claim 29, wherein the halogen or halide compound is reacted with $R2MR1_{4-m}OR3_{m-1}$ in the presence of a catalyst.

31. The method of claim 30, wherein the catalyst is pyridinium hydrochloride.

32. The method of claim 1, wherein m is 3, R2 is fluorinated alkyl, R1 is fluorinated aryl or C4+ alkyl and OR3 is C1–C4 alkoxy.

33. The method of claim 32, wherein R2 is fluorinated vinyl and R1 is fluorinated phenyl.

34. The method of claim 1, wherein m is 3, and R2 is fluorinated alkenyl or fluorinated aryl.

35. The method of claim 34, wherein OR3 is methoxy or ethoxy.

36. The method of claim 35, wherein OR3 is ethoxy.

37. The method of claim 1, wherein the molar ratio of the compound of the general formula $R1_{4-m}MOR3_{m-n}X_n$ to the compound of the general formula R2M1 is from 0.5:1 to 2:1.

38. The method of claim 1, wherein the compound of the general formula $R1_{4-m}MOR3_{m-n}X_n$ is dissolved in ether.

39. The method of claim 1, wherein $R1_{4-m}MOR3_{m-n}X_n$ is prepared by reacting R1X2+Mg+OR3$_4$M, wherein X2 is Br or I, if m is 2 or 3, to form $R1_{4-m}MOR3_m$ followed by reacting $R1_{4-m}MOR3_m$ with a halogen or halogen compound to form $R1_{4-m}MOR3_{m-n}X_n$.

40. The method of claim 39, wherein R1 is single or multi-ring aryl, single or multi-ring fully or partially fluorinated aryl, C5+ alkyl, or fully or partially fluorinated C5+ alkyl.

41. The method of claim 39, wherein X2 is Br.

42. The method of claim 25, wherein m is 2.

43. The method of claim 42, further comprising performing a condensation reaction with the compound of the general formula $R1_{4-m}MOR3_{m-n}X_n$.

44. The method of claim 43, wherein the condensation reaction is performed with H2O or D2O.

45. The method of claim 44, wherein the condensation reaction forms an intermediate $R1_{4-m}MOR3_{m-n}(OD)_n$ or $R1_{4-m}MOR3_{m-n}(OH)_n$.

46. The method of claim 45, wherein a material is formed with a repeating —M—O—M—O— backbone having R2 and R1 substituents on each M and the material having a molecular weight of from 500 to 10000.

47. The method of claim 46, wherein the molecular weight is from 1500 to 5000.

48. The method of claim 1, wherein R2 and R1 are fully fluorinated.

49. The method of claim 44, wherein the condensation reaction is performed with D2O.

50. The method of claim 1, wherein either R2 or R1 is an aryl group that is a single ring or polycyclic aromatic substituent.

51. The method of claim 50, wherein either R2 or R1 is a fully or partially fluorinated single ring or polycyclic aromatic substituent.

52. The method of claim 51, wherein either R2 or R1 has one or two rings.

53. The method of claim 46, further comprising spinning on the material having a molecular weight of from 500 to 10000 onto a substrate.

54. The method of claim 53, further comprising heating the material on the substrate or exposing the material on the substrate to electromagnetic radiation or an electron beam.

55. The method of claim 54, wherein the material is exposed to an electron beam or to electromagnetic radiation via a mask so as to selectively further cross link the material and increase the molecular weight of the material in selected areas.

56. The method of claim 55, further comprising removing non-exposed material with a developer.

57. The method of claim 56, wherein the developer is selected from methanol, ethanol, propanol, acetone, methyl isobutyl ketone, diluted nitric acid, hydrochloric acid, sulfuric acid, HF, aqueous NaOH or KOH solutions.

58. The method of claim 53, wherein the material is spun on after mixing with a solvent.

59. The method of claim 58, wherein the solvent is selected from isopropanol, ethanol, methanol, THF, mesitylene, toluene, cyclohexanone, cyclopentanone, dioxane, methyl isobutyl ketone, or perfluorinated toluene.

60. The method of claim 1, wherein M is Si.

61. The method of claim 58, wherein the material is mixed with a solvent and photoinitiator prior to spin-on.

62. The method of claim 61, wherein the photoinitiator is 1,4-bis(pentafluorobenzoyl)benzene.

63. The method of claim 58, wherein after spin-on, the material is patterned and, along with at least one additional layer deposited on the substrate, formed into a component for an optical device.

64. The method of claim 1, wherein $R1_{4-m}MOR3_m$ and R2M1 are mixed at a temperature less than −40 C.

65. The method of claim 64, wherein $R1_{4-m}MOR3_m$ and R2M1 are mixed at a temperature of between −50 and −100 C.

66. The method of claim 64, wherein $R1_{4-m}MOR3_m$ and R2M1 are mixed in an ether and brought to a temperature over 0 C. during a period of four hours or more.

67. The method of claim 66, wherein $R1_{4-m}MOR3_m$ and R2M1 are brought to room temperature overnight.

68. The method of claim 1, wherein R2 is an aryl group having a single ring or a multi ring structure.

69. The method of claim 68, wherein the single ring or multi ring structure is substituted with one or more groups selected from alkyl, alkenyl and/or alkynyl.

70. The method of claim 69, wherein the one or more substituent groups on the single or multi-ring aryl is at least partially fluorinated.

71. The method of claim 16, wherein M2 is Ge, Al or Sn.

72. The method of claim 1, wherein m is 4.

73. The method of claim 1, wherein m is 3.

74. The method of claim 1, wherein n is 0.

75. The method of claim 1, wherein R1 is nonfluorinated allyl or vinyl.

76. The method of claim 75, wherein R1 is nonfluorinated methyl of vinyl.

77. The method of claim 1, further comprising hydrolyzing and condensing $R2MR1_{3-n}OR3_n$, alone or with another compound of the same formula where M or the R groups are different, so as to form a cross linked material comprising a three dimensional network of M and oxygen atoms with the M atoms having R1 and/or R2 substituents.

78. The method of claim 77, further comprising depositing the cross linked material on a substrate.

79. The method of claim 78, wherein the depositing is by dip coating, spraying or spin coating.

80. The method of claim 79, wherein the substrate is a glass, quartz or semiconductor substrate.

81. The method of claim 79, wherein the substrate is a printed circuit board.

82. The method of claim 78, further comprising providing one or more light emitters or photodetectors on the substrate before or after depositing the cross linked material.

83. The method of claim 78, further comprising exposing the deposited material to electromagnetic radiation or an electron beam to further cross link the material.

84. The method of claim 83, wherein the exposure to electromagnetic radiation is via a mask so as to expose a portion of the material and leave a remaining portion unexposed.

85. The method of claim 84, wherein the unexposed portion of the material is removed with a developer.

86. The method of claim 1, wherein R1 is a fully or partially fluorinated or nonfluorinated alkenyl or alkynyl group.

87. The method of claim 1, wherein R1 is a fully or partially fluorinated or nonfluorinated vinyl or allyl group.

88. The method of claim 1, wherein R1 is a fully or partially fluorinated alkenyl group.

89. The method of claim 1, wherein R2 is a fully or partially fluorinated alkenyl group.

90. The method of claim 1, wherein R1 is a 4 to 8 sided ring structure.

91. The method of claim 90, wherein the 4 to 8 sided ring structure comprises N, S or O.

92. The method of claim 90, wherein R1 is a 5 or 6 sided ring structure.

93. The method of claim 92, wherein R2 is a fully or partially fluorinated phenyl or fluorinated C1–C5 alkyl group.

94. The method of claim 93, wherein the fully or partially fluorinated phenyl group of R2 is substituted with fully or partially fluorinated methyl, vinyl or ethyl groups.

95. The method of claim 1, further comprising purifying $R2MR1_{4-m}OR3_{m-1}$.

96. The method of claim 1, wherein R1 or R2 is an epoxy group.

97. The method of claim 1, wherein R1 or R2 comprises a ring structure or double bond capable of degradation in the presence of an electron beam or in the presence of a photoinitiator and electromagnetic energy.

98. The method of claim 1, wherein m=4 and n=1, such that $MOR3_3X$ is reacted with R2M1 to form $R2MOR3_3$.

99. The method of claim 1, wherein m=3 and n=1, such that $R1MOR3_2X$ is reacted with R2M1 to form $R2MR1OR3_2$.

100. The method of claim 1, wherein n=2.

* * * * *